US012458358B2

(12) United States Patent
Miller et al.

(10) Patent No.: US 12,458,358 B2
(45) Date of Patent: Nov. 4, 2025

(54) METHODS AND SYSTEMS FOR PERFORMING SURGICAL STAPLING

(71) Applicant: Cilag GmbH International, Zug (CH)

(72) Inventors: Christopher C. Miller, Loveland, OH (US); John P. Measamer, Cincinnati, OH (US); Brian F. DiNardo, Cincinnati, OH (US); Richard F. Schwemberger, Cincinnati, OH (US); Johnny H. Alexander, III, West Chester, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/884,865

(22) Filed: Sep. 13, 2024

(65) Prior Publication Data

US 2025/0000512 A1 Jan. 2, 2025

Related U.S. Application Data

(63) Continuation of application No. 18/160,520, filed on Jan. 27, 2023, now Pat. No. 12,102,325, which is a (Continued)

(51) Int. Cl.
*A61B 17/072* (2006.01)
*A61B 17/068* (2006.01)
(Continued)

(52) U.S. Cl.
CPC ........ *A61B 17/1155* (2013.01); *A61B 17/068* (2013.01); *A61B 17/072* (2013.01); (Continued)

(58) Field of Classification Search
CPC ................ A61B 17/068; A61B 17/072; A61B 17/07207; A61B 17/115; A61B 17/1155; (Continued)

(56) References Cited

U.S. PATENT DOCUMENTS

| | | | |
|---|---|---|---|
| 2,211,741 | A | 8/1940 | Elwell |
| 3,974,705 | A | 8/1976 | Wittkamp |

(Continued)

FOREIGN PATENT DOCUMENTS

| | | | |
|---|---|---|---|
| CN | 101596121 | A | 12/2009 |
| CN | 102573663 | A | 7/2012 |

(Continued)

OTHER PUBLICATIONS

Brazilian Examination Report dated Jan. 24, 2022 for Application No. BR 112019009596-9, 4 pgs.

(Continued)

*Primary Examiner* — Scott A Smith

(74) *Attorney, Agent, or Firm* — Frost Brown Todd LLP

(57) ABSTRACT

An apparatus includes a body, a shaft, a stapling head assembly, and an anvil. The body includes a motor, a first user input feature, and a second user input feature. The first user input feature is operable to activate the motor. The shaft extends distally from the body. The stapling head assembly is positioned at a distal end of the shaft. The stapling head assembly includes an anvil coupling feature, at least one annular array of staples, and a staple driver. The second user input feature is operable to drive the anvil coupling feature longitudinally. The staple driver is operable to drive the at least one annular array of staples. The motor is operable to drive the staple driver. The anvil is configured to couple with the anvil coupling feature. The anvil is further configured to deform the staples driven by the staple driver.

20 Claims, 30 Drawing Sheets

Related U.S. Application Data continuation of application No. 17/826,452, filed on May 27, 2022, now Pat. No. 12,029,427, which is a continuation of application No. 16/836,291, filed on Mar. 31, 2020, now Pat. No. 11,446,036, which is a continuation of application No. 15/604,787, filed on May 25, 2017, now Pat. No. 10,709,452, which is a continuation-in-part of application No. 15/581,640, filed on Apr. 28, 2017, now Pat. No. 10,729,444, and a continuation-in-part of application No. 15/581,546, filed on Apr. 28, 2017, now Pat. No. 10,695,068, and a continuation-in-part of application No. 15/350,513, filed on Nov. 14, 2016, now Pat. No. 10,980,542, and a continuation-in-part of application No. 15/350,621, filed on Nov. 14, 2016, now abandoned, and a continuation-in-part of application No. 14/751,612, filed on Jun. 26, 2015, now Pat. No. 10,478,189, and a continuation-in-part of application No. 14/033,688, filed on Sep. 23, 2013, now abandoned, and a continuation-in-part of application No. 14/033,751, filed on Sep. 23, 2013, now Pat. No. 9,907,552.

(51) Int. Cl.
*A61B 17/115* (2006.01)
*A61B 17/00* (2006.01)

(52) U.S. Cl.
CPC .................. *A61B 17/07207* (2013.01); *A61B 2017/00115* (2013.01); *A61B 2017/00199* (2013.01); *A61B 2017/00221* (2013.01); *A61B 2017/00367* (2013.01); *A61B 2017/00398* (2013.01); *A61B 2017/00734* (2013.01); *A61B 2017/07214* (2013.01); *A61B 2017/07228* (2013.01); *A61B 2017/07264* (2013.01); *A61B 2017/07271* (2013.01)

(58) Field of Classification Search
CPC .......... A61B 2017/00017; A61B 2017/00115; A61B 2017/00199; A61B 2017/00367; A61B 2017/00398; A61B 2017/00477; A61B 2017/07214; A61B 2017/07264; A61B 2017/07271; A61B 2017/07228
USPC .............. 227/19, 175.1, 175.2, 176.1, 180.1; 606/1, 139, 219
See application file for complete search history.

(56) References Cited

U.S. PATENT DOCUMENTS

| | | | |
|---|---|---|---|
| 4,289,041 | A | 9/1981 | Valdespino |
| 4,319,576 | A | 3/1982 | Rothfuss et al. |
| 4,644,952 | A | 2/1987 | Patipa et al. |
| 4,805,823 | A | 2/1989 | Rothfuss |
| 5,205,459 | A | 4/1993 | Brinkerhoff et al. |
| 5,271,544 | A | 12/1993 | Fox et al. |
| 5,275,322 | A | 1/1994 | Wolf et al. |
| 5,285,945 | A | 2/1994 | Brinkerhoff et al. |
| 5,292,053 | A | 3/1994 | Smith et al. |
| 5,333,773 | A | 8/1994 | Main et al. |
| 5,337,623 | A | 8/1994 | Huang et al. |
| 5,350,104 | A | 9/1994 | Main et al. |
| 5,350,400 | A | 9/1994 | Esposito et al. |
| 5,415,334 | A | 5/1995 | Williamson, IV et al. |
| 5,465,895 | A | 11/1995 | Knodel et al. |
| 5,533,661 | A | 7/1996 | Main et al. |
| 5,571,285 | A | 11/1996 | Chow et al. |
| 5,597,107 | A | 1/1997 | Knodel et al. |
| 5,628,446 | A | 5/1997 | Geiste et al. |
| 5,632,432 | A | 5/1997 | Schulze et al. |
| 5,673,840 | A | 10/1997 | Schulze |
| 5,704,534 | A | 1/1998 | Huitema et al. |
| 5,814,055 | A | 9/1998 | Knodel et al. |
| 6,021,573 | A | 2/2000 | Kikuchi et al. |
| 6,050,472 | A | 4/2000 | Shibata |
| 6,058,815 | A | 5/2000 | Habermehl |
| 6,443,973 | B1 | 9/2002 | Whitman |
| 6,471,713 | B1 | 10/2002 | Vargas et al. |
| 6,698,177 | B1 | 3/2004 | Akehi et al. |
| 6,945,444 | B2 | 9/2005 | Gresham et al. |
| 6,978,921 | B2 | 12/2005 | Shelton, IV et al. |
| 7,000,818 | B2 | 2/2006 | Shelton, IV et al. |
| 7,143,923 | B2 | 12/2006 | Shelton, IV et al. |
| 7,303,108 | B2 | 12/2007 | Shelton, IV et al. |
| 7,367,485 | B2 | 5/2008 | Shelton, IV et al. |
| 7,380,695 | B2 | 6/2008 | Doll et al. |
| 7,380,696 | B2 | 6/2008 | Shelton, IV et al. |
| 7,398,907 | B2 | 7/2008 | Racenet et al. |
| 7,404,508 | B2 | 7/2008 | Smith et al. |
| 7,422,136 | B1 | 9/2008 | Marczyk |
| 7,434,715 | B2 | 10/2008 | Shelton, IV et al. |
| 7,556,185 | B2 | 7/2009 | Viola |
| 7,721,930 | B2 | 5/2010 | McKenna et al. |
| 7,722,610 | B2 | 5/2010 | Viola et al. |
| 7,770,775 | B2 | 8/2010 | Shelton, IV et al. |
| 7,794,475 | B2 | 9/2010 | Hess et al. |
| 7,815,092 | B2 | 10/2010 | Whitman et al. |
| 7,959,050 | B2 | 6/2011 | Smith et al. |
| 8,025,199 | B2 | 9/2011 | Whitman et al. |
| 8,056,789 | B1 | 11/2011 | White et al. |
| 8,141,762 | B2 | 3/2012 | Bedi et al. |
| 8,360,296 | B2 | 1/2013 | Zingman |
| 8,397,832 | B2 | 3/2013 | Blickle et al. |
| 8,408,439 | B2 | 4/2013 | Huang et al. |
| 8,413,870 | B2 | 4/2013 | Pastorelli et al. |
| 8,453,914 | B2 | 6/2013 | Laurent et al. |
| 8,579,178 | B2 | 11/2013 | Holsten et al. |
| 8,636,193 | B2 | 1/2014 | Whitman et al. |
| 8,800,838 | B2 | 8/2014 | Shelton, IV et al. |
| 8,910,847 | B2 | 12/2014 | Nalagatla et al. |
| 8,998,061 | B2 | 4/2015 | Williams et al. |
| 9,161,803 | B2 | 10/2015 | Yates et al. |
| 9,232,945 | B2 | 1/2016 | Zingman |
| 9,289,207 | B2 | 3/2016 | Shelton, IV |
| 9,463,022 | B2 | 10/2016 | Swayze et al. |
| 9,498,222 | B2 | 11/2016 | Scheib et al. |
| 9,517,070 | B2 | 12/2016 | Mulreed |
| 9,532,783 | B2 | 1/2017 | Swayze et al. |
| 9,561,030 | B2 | 2/2017 | Zhang et al. |
| 9,572,573 | B2 | 2/2017 | Scheib et al. |
| 9,597,081 | B2 | 3/2017 | Swayze et al. |
| 9,713,469 | B2 | 7/2017 | Leimbach et al. |
| 9,724,100 | B2 | 8/2017 | Scheib et al. |
| 9,750,502 | B2 | 9/2017 | Scirica et al. |
| 9,907,552 | B2 | 3/2018 | Measamer et al. |
| 9,936,949 | B2 | 4/2018 | Measamer et al. |
| 10,076,325 | B2 | 9/2018 | Huang et al. |
| 10,092,292 | B2 | 10/2018 | Boudreaux et al. |
| 10,159,482 | B2 | 12/2018 | Swayze et al. |
| 10,188,386 | B2 | 1/2019 | Measamer et al. |
| 10,194,911 | B2 | 2/2019 | Miller et al. |
| 10,226,253 | B2 | 3/2019 | DiNardo et al. |
| 10,265,066 | B2 | 4/2019 | Measamer et al. |
| 10,271,841 | B2 | 4/2019 | Overmyer et al. |
| 10,271,842 | B2 | 4/2019 | Fox et al. |
| 10,307,157 | B2 | 6/2019 | Miller et al. |
| 10,327,776 | B2 | 6/2019 | Harris et al. |
| 10,405,855 | B2 | 9/2019 | Stager et al. |
| 10,456,134 | B2 | 10/2019 | DiNardo et al. |
| 10,478,189 | B2 | 11/2019 | Bear et al. |
| 10,485,548 | B2 | 11/2019 | Miller et al. |
| 10,542,981 | B2 | 1/2020 | Miller et al. |
| 10,603,041 | B2 | 3/2020 | Miller et al. |
| 10,695,068 | B2 | 6/2020 | Kluener et al. |
| 10,709,452 | B2 * | 7/2020 | DiNardo .......... A61B 17/07207 |
| 10,729,444 | B2 | 8/2020 | Stager et al. |
| 10,905,415 | B2 | 2/2021 | DiNardo et al. |
| 10,959,724 | B2 | 3/2021 | Miller et al. |
| 10,980,542 | B2 | 4/2021 | Miller et al. |
| 11,446,036 | B2 | 9/2022 | DiNardo et al. |

(56) References Cited

U.S. PATENT DOCUMENTS

| | | | | |
|---|---|---|---|---|
| 12,029,427 | B2 * | 7/2024 | DiNardo | A61B 17/068 |
| 12,102,325 | B2 * | 10/2024 | DiNardo | A61B 17/1155 |
| 2007/0175955 | A1 | 8/2007 | Shelton, IV | |
| 2007/0194082 | A1 | 8/2007 | Morgan et al. | |
| 2009/0108048 | A1 | 4/2009 | Zemlok et al. | |
| 2009/0270895 | A1 | 10/2009 | Churchill et al. | |
| 2011/0087276 | A1 | 4/2011 | Bedi et al. | |
| 2012/0083836 | A1 | 4/2012 | Shelton, IV | |
| 2012/0264193 | A1 | 10/2012 | Kuwana et al. | |
| 2014/0103091 | A1 | 4/2014 | Whitman et al. | |
| 2014/0158747 | A1 | 6/2014 | Measamer et al. | |
| 2014/0305992 | A1 | 10/2014 | Kimsey et al. | |
| 2015/0083772 | A1 | 3/2015 | Miller et al. | |
| 2015/0108198 | A1 | 4/2015 | Estrella | |
| 2015/0297222 | A1 | 10/2015 | Huitema et al. | |
| 2015/0297225 | A1 | 10/2015 | Huitema et al. | |
| 2015/0324317 | A1 | 11/2015 | Collins et al. | |
| 2018/0132849 | A1 | 5/2018 | Miller et al. | |
| 2021/0068829 | A1 | 3/2021 | Miller et al. | |
| 2022/0110630 | A1 | 4/2022 | Miller et al. | |

FOREIGN PATENT DOCUMENTS

| | | | |
|---|---|---|---|
| CN | 103764046 | A | 4/2014 |
| CN | 205198062 | U | 5/2016 |
| EP | 1992296 | A1 | 11/2008 |
| EP | 2025293 | A1 | 2/2009 |
| EP | 2962647 | A1 | 1/2016 |
| JP | 2009-045450 | A | 3/2009 |
| RU | 2009105055 | A | 8/2010 |
| WO | 03/079911 | A1 | 10/2003 |

OTHER PUBLICATIONS

Brazilian Office Action dated Feb. 14, 2020 for Application No. BR112016006337-6, 4 pgs.

Chinese Search Report dated Sep. 13, 2021, for Application No. 201780070473.0, 3 pgs.

Chinese Office Action. The First Office Action, dated Sep. 18, 2021, for Application No. CN 201780070473.0, 12 pgs.

Chinese Office Action, The Second Office Action, dated Mar. 21, 2022, for Application No. CN 201780070473.0, 11 pgs.

Chinese Office Action, The Third Office Action, dated Sep. 30, 2022, for Application No. CN 201780070473.0, 11 pgs.

Chinese Search Report, First Search, dated Feb. 24, 2018 for Application No. CN 201480052189.7, 2 pgs.

Chinese Office Action, The Second Office Action, dated Nov. 23, 2018 for Application No. CN 201480052189.7, 4 pgs.

European Search Report and Written Opinion dated Feb. 10, 2015 for Application No. EP 14185807.6, 8 pgs.

European Exam Report dated Feb. 29, 2016 for Application No. EP 14185807.6, 5 pgs.

European Communication, Intention to Grant, dated Mar. 30, 2017 for Application No. EP 14185807.6, 125 pgs.

European Search Report and Written Opinion dated Apr. 24, 2018, for Application No. EP 17201431.8, 6 pgs.

European Examination Report dated Feb. 23, 2022, for Application No. EP 17201431.8, 3 pgs.

Indian Office Action dated Sep. 14, 2020 for Application No. IN 201617011060, 7 pgs.

Indian Examination Report dated Aug. 10, 2021, for Application No. IN 201917018244, 6 pgs.

International Search Report and Written Opinion dated Dec. 22, 2014 for Application No. PCT/US2014/056514, 11 pgs.

International Search Report and Written Opinion dated Sep. 4, 2017, for International Application No. PCT/US2017/035117, 9 pgs.

Japanese Office Action, Notification of Reasons for Refusal, and Search Report by Registered Searching Organization dated May 8, 2018 for Application No. JP 2016-544011, 21 pgs.

Japanese Office Action, Decision to Grant a Patent, dated Jul. 24, 2018 for Application No. JP 2016-544011, 3 pgs.

Japanese Notification of Reasons for Refusal dated Mar. 17, 2021, for Application No. JP 2019-524876, 9 pgs.

Russian Office Action and Search Report dated May 14, 2018 for Application No. RU 2016115744, 9 pgs.

* cited by examiner

METHODS AND SYSTEMS FOR PERFORMING SURGICAL STAPLING

PRIORITY

This application is a continuation of Ser. No. 18/160,520, filed Jan. 27, 2023, issued as U.S. Pat. No. 12,102,325 on Oct. 1, 2024, which is a continuation of U.S. patent application Ser. No. 17/826,452, filed May 27, 2022, issued as U.S. Pat. No. 12,029,427 on Jul. 9, 2024, which is a continuation of U.S. patent application Ser. No. 16/836,291, filed Mar. 31, 2020, issued as U.S. Pat. No. 11,446,036 on Sep. 20, 2022, which is a continuation of U.S. patent application Ser. No. 15/604,787, filed May 25, 2017, issued as U.S. Pat. No. 10,709,452 on Jul. 14, 2020, the disclosures of which are incorporated by reference herein in their entireties.

The '787 application is a continuation-in-part of U.S. patent application Ser. No. 14/033,688, entitled "Surgical Stapler with Rotary Cam Drive and Return," filed Sep. 23, 2013, published as U.S. Pub. No. 2015/0083772 on Mar. 26, 2015, now abandoned, the disclosure of which is incorporated by reference herein in its entirety.

The '787 application is also a continuation-in-part of U.S. patent application Ser. No. 14/033,751, entitled "Control Features for Motorized Surgical Stapling Instrument," filed Sep. 23, 2013, issued as U.S. Pat. No. 9,907,552 on Mar. 6, 2018, the disclosure of which is incorporated by reference herein in its entirety.

The '787 application is also a continuation-in-part of U.S. patent application Ser. No. 14/751,612, entitled "Method of Applying an Annular Array of Staples to Tissue," filed Jun. 26, 2015, issued as U.S. Pat. No. 10,478,189 on Nov. 19, 2019, the disclosure of which is incorporated by reference herein in its entirety.

The '787 application is also a continuation-in-part of U.S. patent application Ser. No. 15/350,513, entitled "Circular Stapler with Recessed Deck," filed Nov. 14, 2016, issued as U.S. Pat. No. 10,980,542 on Apr. 20, 2021, the disclosure of which is incorporated by reference herein in its entirety.

The '787 application is also a continuation-in-part of U.S. patent application Ser. No. 15/350,621, entitled "Staple Forming Pocket Configurations for Circular Surgical Stapler Anvil," filed Nov. 14, 2016, published as U.S. Pub. No. 2018/0132849 on May 17, 2018, now abandoned, the disclosure of which is incorporated by reference herein in its entirety.

The '787 application is also a continuation-in-part of U.S. patent application Ser. No. 15/581,546, entitled "Hysteresis Removal Feature in Surgical Stapling Instrument," filed Apr. 28, 2017, issued as U.S. Pat. No. 10,695,068 on Jun. 30, 2020, the disclosure of which is incorporated by reference herein in its entirety.

The '787 application is also a continuation-in-part of U.S. patent application Ser. No. 15/581,640, entitled "Liquid-Immune Trigger Circuit for Surgical Instrument," filed Apr. 28, 2017, issued as U.S. Pat. No. 10,729,444 on Aug. 4, 2020, the disclosure of which is incorporated by reference herein in its entirety.

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis, an end-to-side anastomosis, or a side-to-side anastomosis. The anastomosis may provide a substantially unobstructed flow path from one portion of the digestive tract to the other portion of the digestive tract, without also providing any kind of leaking at the site of the anastomosis.

One example of an instrument that may be used to provide an anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
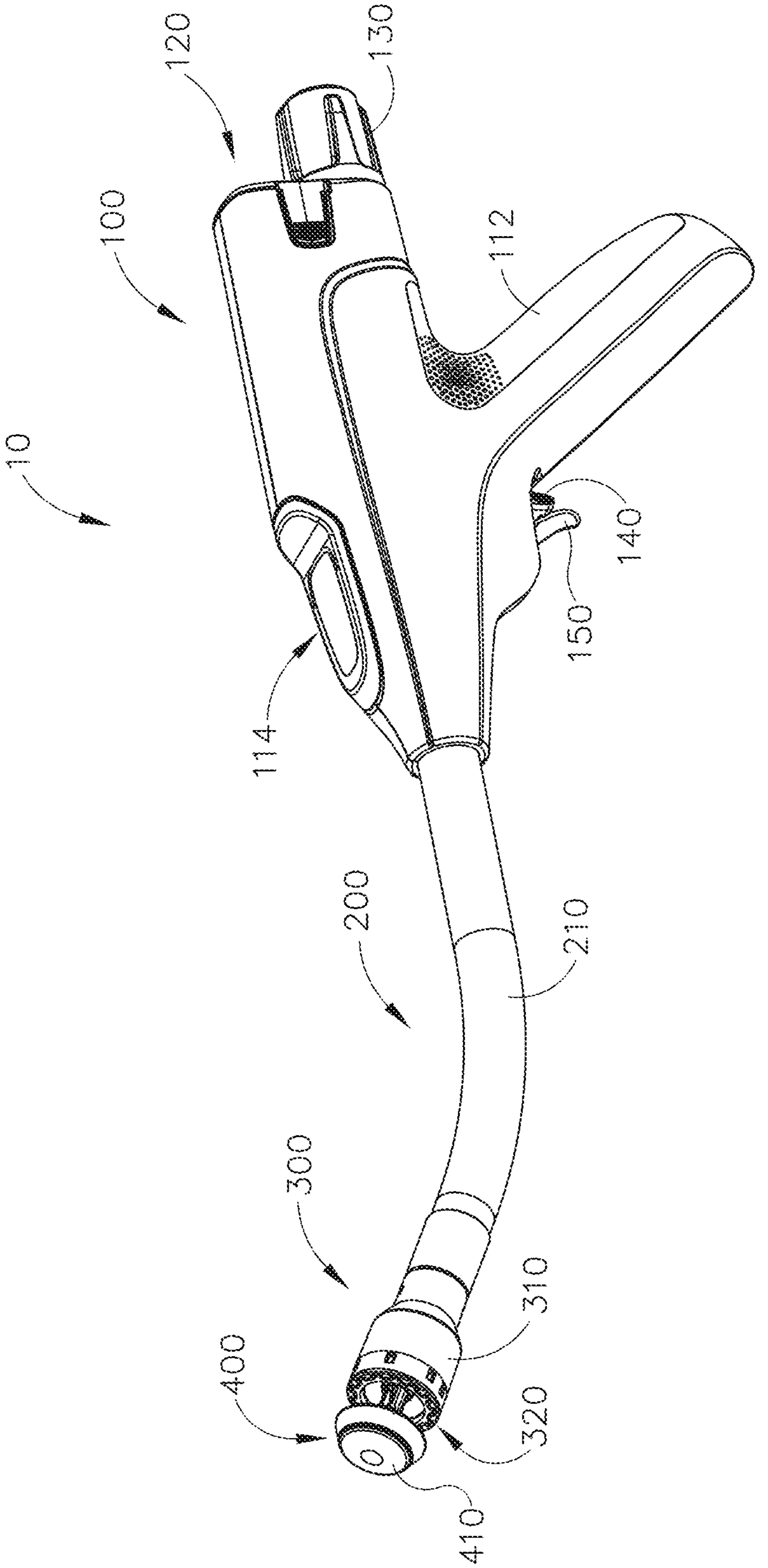
FIG. 1 depicts a perspective view of an illustrative circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Illustrative Circular Stapling Surgical Instrument

Figure 2:
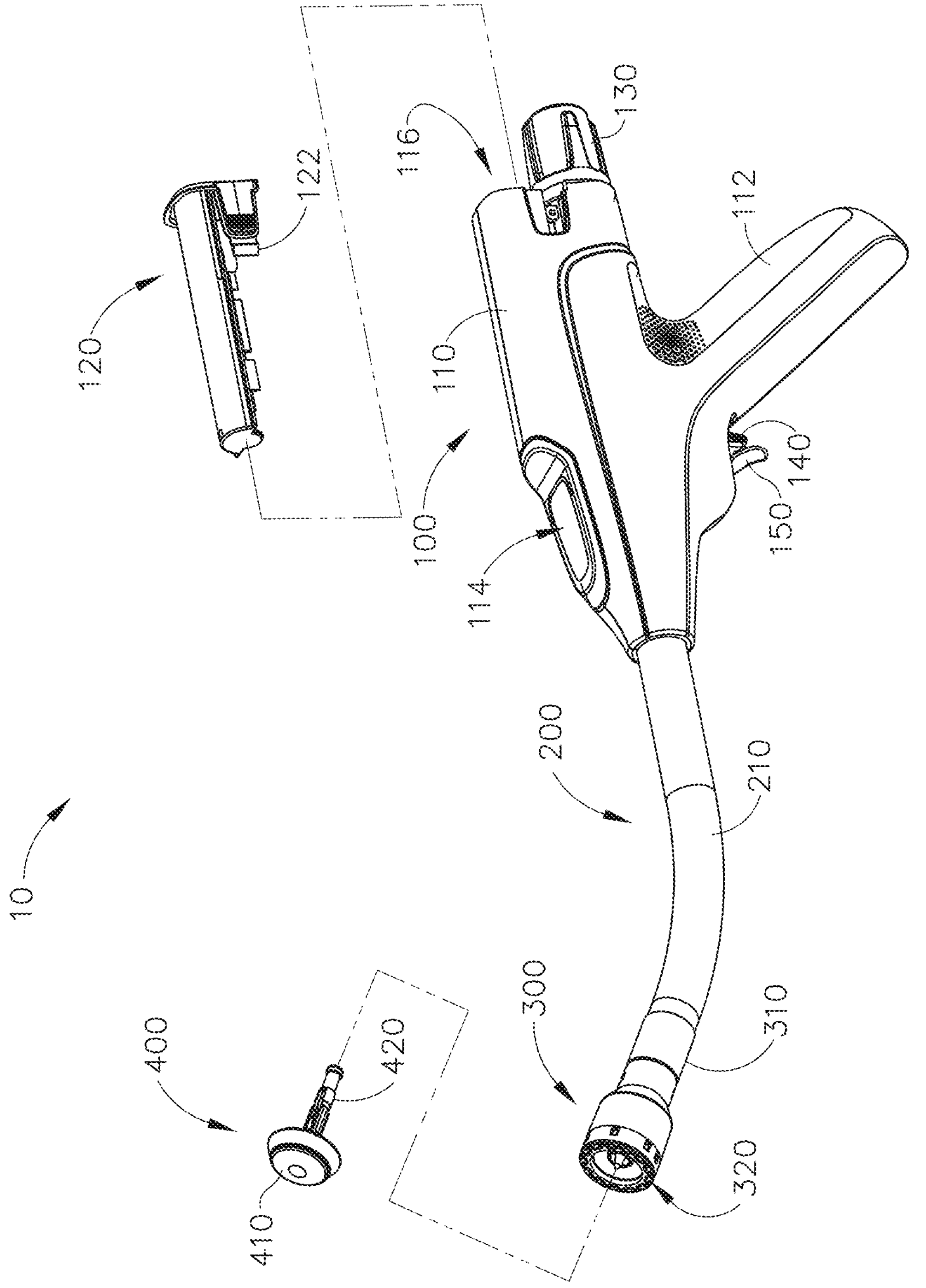
FIG. 2 depicts a perspective view of the circular stapler of FIG. 1, with a battery pack removed from a handle assembly and an anvil removed from a stapling head assembly.

FIGS. 1-2 depict an illustrative surgical circular stapling instrument (10) that may be used to provide an end-to-end, side-to-side, or end-to-side anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (100) further includes a user feedback feature (114) that permits viewing of a movable indicator needle (1526) as will be described in greater detail below. In some versions, a series of hash marks, colored regions, and/or other fixed indicators are positioned adjacent to user feedback feature (114) in order to provide a visual context for indicator needle (1526), thereby facilitating operator evaluation of the position of needle (1526) within user feedback feature (114). Various suitable alternative features and configurations for handle assembly (112) will be apparent to those of ordinary skill in the art in view of the teachings herein.

Instrument (10) of the present example further includes a battery pack (120). Battery pack (120) is operable to provide electrical power to a motor (160) in pistol grip (112) as will be described in greater detail below. Battery pack (120) is removable from handle assembly (100). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. To remove battery pack (120), the operator may press latches (122) inwardly to disengage latches (122) from the interior features of casing (110) then pull battery pack (120) proximally from socket (116). It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). It should also be understood that, in some versions, battery pack (120) is unitarily incorporated within handle assembly (100) such that battery back (120) cannot be removed from handle assembly (100).

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various illustrative components that may be incorporated into shaft assembly (100) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

II. Illustrative Anvil

A. Overview

In the following discussion of anvil (400), the terms "distal" and "proximal" (and variations thereof) will be used with reference to the orientation of anvil (400) when anvil (400) is coupled with shaft assembly (200) of instrument (10). Thus, proximal features of anvil (400) will be closer to the operator of instrument (10); while distal features of anvil (400) will be further from the operator of instrument (10).

Figure 3:
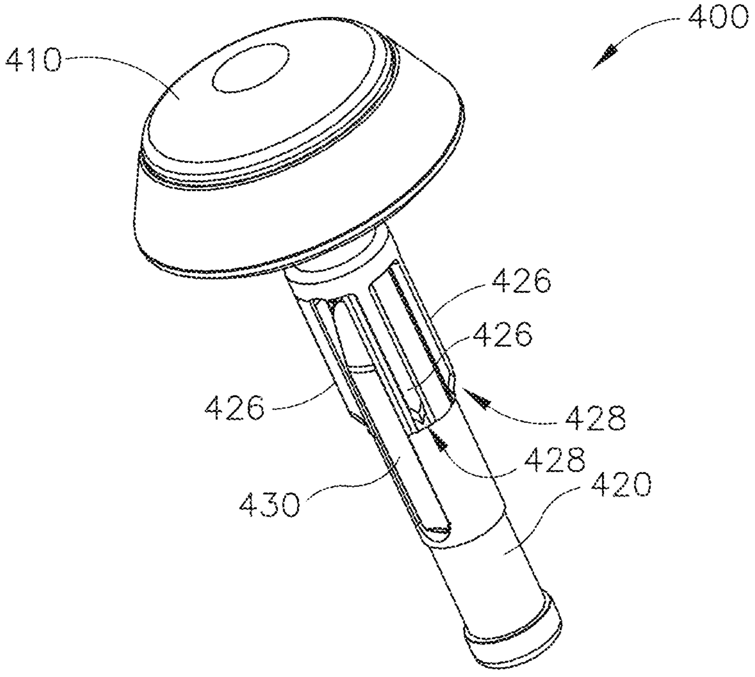
FIG. 3 depicts a perspective view of the anvil of the circular stapler of FIG. 1.
Figure 4:
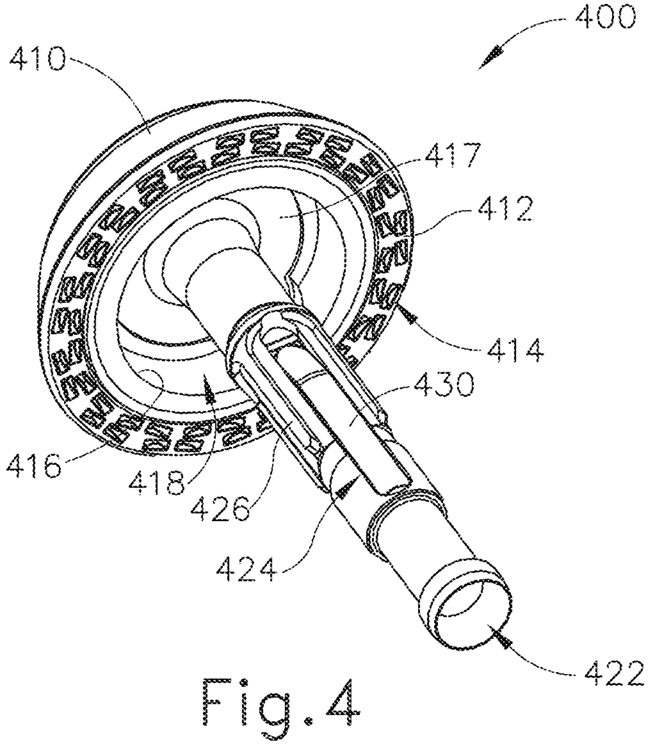
FIG. 4 depicts another perspective view of the anvil of FIG. 3.
Figure 5:
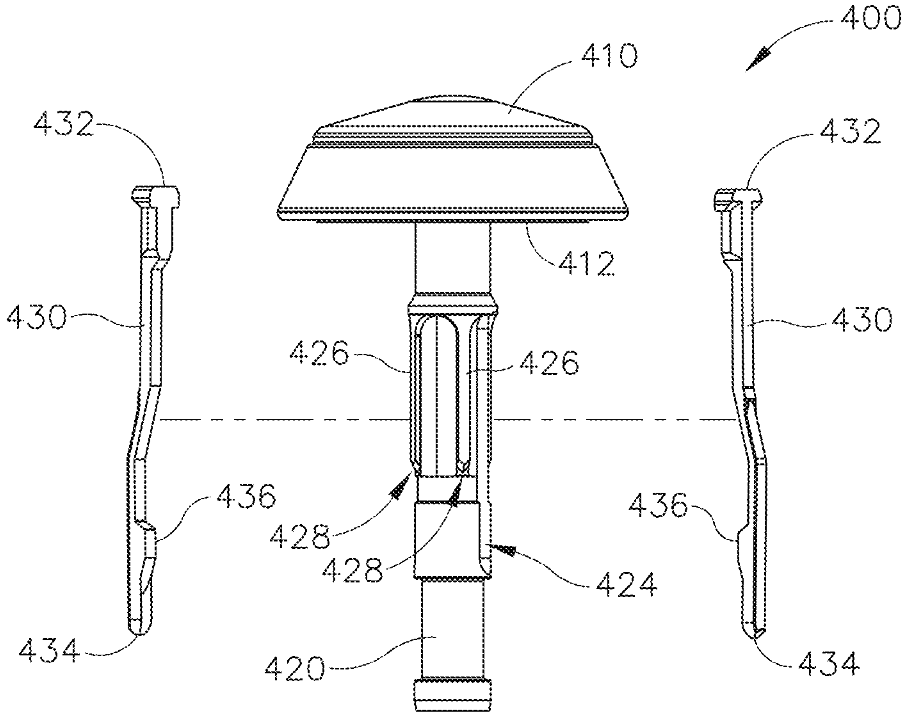
FIG. 5 depicts an exploded side elevational view of the anvil of FIG. 3.

As best seen in FIGS. 3-5, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 5, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to pivot radially inwardly toward the longitudinal axis defined by shank (420). Latch members (430)

thus act as retaining clips. This allows anvil (400) to be removably secured to a trocar (330) of stapling head assembly (300) as will be described in greater detail below. When shank (420) is secured to trocar (330) and trocar (330) is retracted proximally, the inner diameter of bore (314) in inner core member (312) of body member (310) laterally constrains latch members (430) to maintain engagement between latch shelves (436) and proximal surface (338) of head (334) of trocar (330). This engagement prevents anvil (400) from being released from trocar (330) during firing of stapling head assembly (300). It should be understood, however, that latch members (436) are merely optional. Anvil (400) may be removably secured to a trocar (330) using any other suitable components, features, or techniques.

As best seen in FIGS. 3-4, shank (420) of the present example includes a set of longitudinally extending splines (426) that are spaced about shank (420) in an angular array. The proximal end of each spline (426) includes a respective lead-in edge (428). As described in greater detail below, splines (426) are configured to engage corresponding splines (316) of an inner body member (310) of stapling head assembly (300) in order to consistently provide a predetermined angular alignment between anvil (400) and stapling head assembly (300). As also described below, this angular alignment may ensure that staple forming pockets (414) of anvil (400) are consistently angularly aligned appropriately with staple openings (324) of stapling head assembly (300). Thus, in the present example, splines (426) are precisely and consistently positioned in relation to staple forming pockets (414). In versions where head (410) and shank (420) are initially formed as separate pieces and then later joined together, the machine or other device that is used to join head (410) and shank (420) together may have appropriate indexing capabilities in order to reliably and consistently achieve the proper angular positioning of head (410) and shank (420) to thereby provide precise and consistent positioning of splines (426) in relation to staple forming pockets (414). Various suitable ways in which such results may be achieved will be apparent to those of ordinary skill in the art in view of the teachings herein. In some other versions, head (410) and shank (420) are formed together simultaneously, as a single unitary construction.

In some instances, it may be desirable to change the configuration and arrangement of staple forming pockets (414) in anvil (400). It should be understood that reconfiguring and rearranging staple forming pockets (414) may result in reconfiguration and rearrangement of staples (90) that are formed by staple forming pockets (414). For instance, the configuration and arrangement of staple forming pockets (414) may affect the structural integrity of an anastomosis (70) that is secured by staples (90). In addition, the configuration and arrangement of staple forming pockets (414) may affect the hemostasis that is achieved at an anastomosis (70) that is secured by staples (90). The following description relates to several illustrative variations of anvil (400), providing staple forming pocket configurations and arrangements that differ from those of staple forming pockets (414).

It should be understood that the various alternatives to anvil (400) described below may be readily used with instrument (10), in place of anvil (400). It should also be understood that, in some instances, the configuration and arrangement of staple openings (324) in deck member (320) may need to be varied in order to complement the configuration and arrangement of the alternative staple forming pockets described below. Various suitable ways in which the alternatives to anvil (400) described below may be incorporated into instrument (10) will be apparent to those of ordinary skill in the art in view of the teachings herein.

B. Illustrative Three-Dimensional Staple Formation Features

Figure 6:
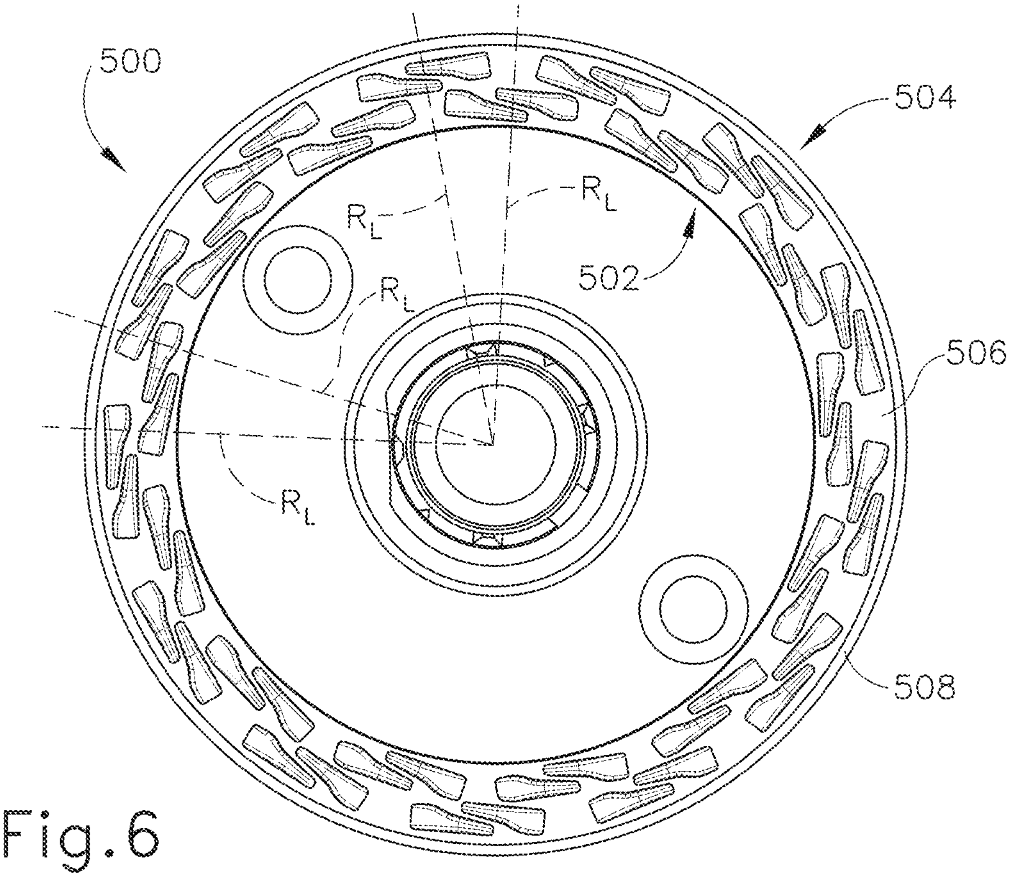
FIG. 6 depicts a bottom plan view of an illustrative alternative anvil that may be used with the circular stapler of FIG. 1 in place of the anvil of FIG. 3.
Figure 7:
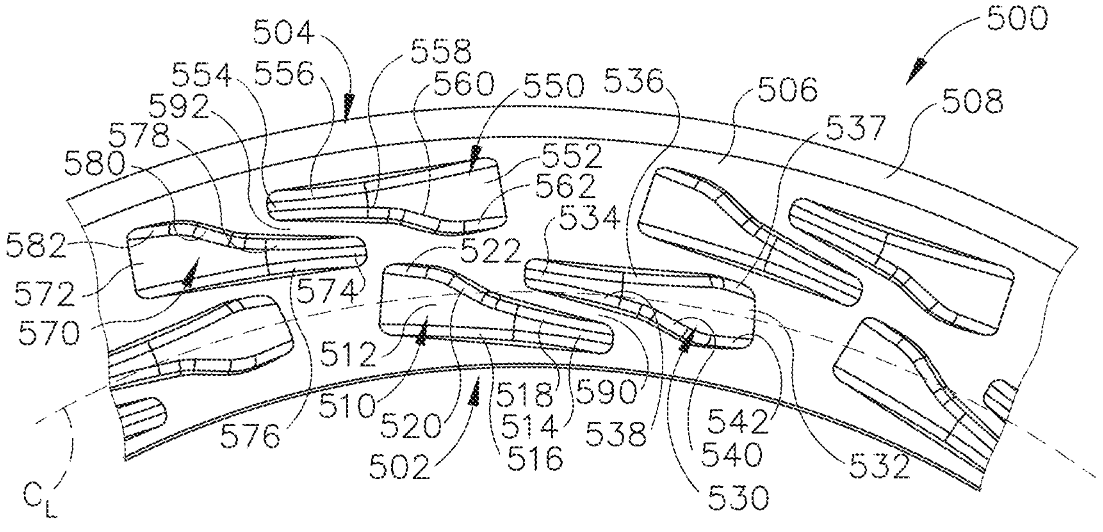
FIG. 7 depicts an enlarged bottom plan view of a portion of the anvil of FIG. 6.
Figure 8:
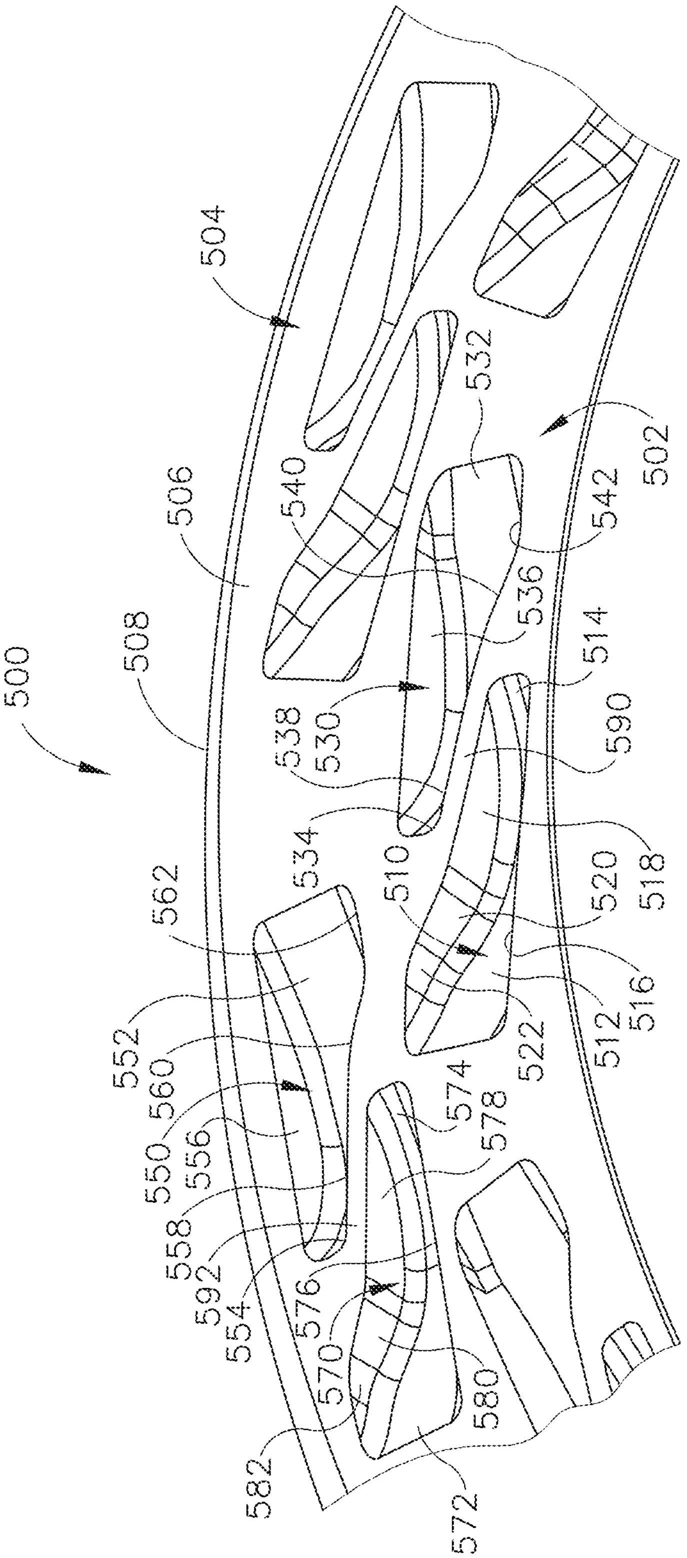
FIG. 8 depicts an enlarged perspective view of a portion of the anvil of FIG. 6.

FIGS. 6-8 show an illustrative alternative anvil (500) that may be used with a modified version of instrument (10). Anvil (500) of this example is configured and operable just like anvil (400), except for the differences described below. Anvil (500) of the present example comprises a proximal surface (506) that defines an inner annular array (502) of staple forming pockets (510, 530) and an outer annular array (504) of staple forming pockets (550, 570). A chamfered edge (508) extends about the outer perimeter of proximal surface (506). It should be understood that anvil (500) may be secured to trocar (330), that proximal surface (506) may be used to compress tissue against deck surface (322), and that staple driver (352) may drive staples (90) through tissue into staple forming pockets (510, 530, 550, 570) in order to thereby form staples (90) in the tissue.

As best seen in FIGS. 7-8, each staple forming pocket (510) comprises a staple entry surface (512) and a staple exit surface (514). Surfaces (512, 514) are contiguous with each other and define a concave recess. The concave recess formed by surfaces (512, 514) is further defined by an inner wall (516), a first outer wall (518), a second outer wall (520), and a third outer wall (522). In the present example, walls (516, 518, 520, 522) are each substantially flat. Wall (518) defines a relatively narrow, tapered gap with wall (516). Wall (522) defines a relatively wide gap with wall (516). Wall (520) is obliquely angled, providing an inwardly sloped transition from wall (522) to wall (518). Thus, walls (518, 520, 522) together provide a dogleg configuration. The edge connecting wall (516) with wall (522) is substantially straight in this example. Similarly, the edge connecting wall (516) with wall (518) is substantially straight in this example.

It should be understood that when a first leg of staple (90) is driven into staple forming pocket (510), the first leg first encounters staple entry surface (512), bends generally toward the second leg of staple (90) along a first plane that is orthogonal to the axis of the unformed first leg, and then bends proximally back generally toward the crown of staple (90). In addition, the first leg will eventually encounter wall (520), which will provide a cam surface bending the first leg along a second plane that is orthogonal to the axis of the unformed first leg. In particular, wall (520) and then wall (518) will deflect the first leg radially inwardly toward the central axis of anvil (500). Thus, staple forming pocket (510) will ultimately deflect a first leg of a staple (90) proximally and radially inwardly. Wall (516) will restrict the degree to which the first leg of staple (90) deflects radially inwardly.

Each staple forming pocket (530) comprises a staple entry surface (532) and a staple exit surface (534). Surfaces (532, 534) are contiguous with each other and define a concave recess. The concave recess formed by surfaces (532, 534) is further defined by an outer wall (536), a first inner wall (538), a second inner wall (540), and a third inner wall (542). In the present example, walls (536, 538, 540, 542) are each substantially flat. Wall (538) defines a relatively narrow, tapered gap with wall (536). Wall (542) defines a relatively wide gap with wall (536). Wall (540) is obliquely angled, providing an outwardly sloped transition from wall (542) to wall (538). Thus, walls (538, 540, 542) together provide a dogleg configuration. The edge connecting wall (536) with wall (542) is substantially straight in this example. Similarly, the edge connecting wall (536) with wall (538) is substantially straight in this example.

It should be understood that when a second leg of staple (90) is driven into staple forming pocket (530), the second leg first encounters staple entry surface (532), bends generally toward the first leg of staple (90) along a first plane that is orthogonal to the axis of the unformed second leg, and then bends proximally back generally toward the crown of staple (90). In addition, the second leg will eventually encounter wall (540), which will provide a cam surface bending the second leg along a second plane that is orthogonal to the axis of the unformed second leg. In particular, wall (540) and then wall (538) will deflect the second leg radially outwardly away from the central axis of anvil (500). Thus, staple forming pocket (530) will ultimately deflect a second leg of a staple (90) proximally and radially outwardly. Wall (536) will restrict the degree to which the second leg of staple (90) deflects radially outwardly.

Each staple forming pocket (550) comprises a staple entry surface (552) and a staple exit surface (554). Surfaces (552, 554) are contiguous with each other and define a concave recess. The concave recess formed by surfaces (552, 554) is further defined by an outer wall (556), a first inner wall (558), a second inner wall (560), and a third inner wall (562). In the present example, walls (556, 558, 560, 562) are each substantially flat. Wall (558) defines a relatively narrow, tapered gap with wall (556). Wall (562) defines a relatively wide gap with wall (556). Wall (560) is obliquely angled, providing an outwardly sloped transition from wall (562) to wall (558). Thus, walls (558, 560, 562) together provide a dogleg configuration. The edge connecting wall (556) with wall (562) is substantially straight in this example. Similarly, the edge connecting wall (556) with wall (558) is substantially straight in this example.

It should be understood that when a second leg of staple (90) is driven into staple forming pocket (550), the second leg first encounters staple entry surface (552), bends generally toward the first leg of staple (90) along a first plane that is orthogonal to the axis of the unformed second leg, and then bends proximally back generally toward the crown of staple (90). In addition, the second leg will eventually encounter wall (560), which will provide a cam surface bending the second leg along a second plane that is orthogonal to the axis of the unformed second leg. In particular, wall (560) and then wall (558) will deflect the second leg radially outwardly away from the central axis of anvil (500). Thus, staple forming pocket (550) will ultimately deflect a second leg of a staple (90) proximally and radially outwardly. Wall (556) will restrict the degree to which the second leg of staple (90) deflects radially outwardly.

Each staple forming pocket (570) comprises a staple entry surface (572) and a staple exit surface (574). Surfaces (572, 574) are contiguous with each other and define a concave recess. The concave recess formed by surfaces (572, 574) is further defined by an inner wall (576), a first outer wall (578), a second outer wall (580), and a third outer wall (582). In the present example, walls (576, 578, 580, 582) are each substantially flat. Wall (578) defines a relatively narrow, tapered gap with wall (576). Wall (582) defines a relatively wide gap with wall (576). Wall (580) is obliquely angled, providing an inwardly sloped transition from wall (582) to wall (578). Thus, walls (578, 580, 582) together provide a dogleg configuration. The edge connecting wall (576) with wall (582) is substantially straight in this example. Similarly, the edge connecting wall (576) with wall (578) is substantially straight in this example.

It should be understood that when a first leg of staple (90) is driven into staple forming pocket (570), the first leg first encounters staple entry surface (572), bends generally toward the second leg of staple (90) along a first plane that is orthogonal to the axis of the unformed first leg, and then bends proximally back generally toward the crown of staple (90). In addition, the first leg will eventually encounter wall (580), which will provide a cam surface bending the first leg along a second plane that is orthogonal to the axis of the unformed first leg. In particular, wall (580) and then wall (578) will deflect the first leg radially inwardly toward the central axis of anvil (500). Thus, staple forming pocket (570) will ultimately deflect a first leg of a staple (90) proximally and radially inwardly. Wall (576) will restrict the degree to which the first leg of staple (90) deflects radially inwardly.

As best seen in FIG. 6, staple forming pockets (510, 530, 550, 570) are arranged such that a radius line ($R_L$) extending outwardly from the center of anvil (500) passes through the region of entry surface (512) of staple forming pocket (510) and through the region of entry surface (552) of staple forming pocket (550). Thus, staple forming pockets (510, 550) overlap along a radial dimension. In addition, another radius line ($R_L$) extending outwardly from the center of anvil (500) passes through the region of entry surface (532) of staple forming pocket (530) and through the region of entry surface (572) of staple forming pocket (570). Thus, staple forming pockets (530, 570) overlap along a radial dimension. In addition, another radius line ($R_L$) extending outwardly from the center of anvil (500) passes through the region of exit surface (574) of staple forming pocket (570) and through the region of exit surface (554) of staple forming pocket (550). Thus, staple forming pockets (550, 570) overlap along a radial dimension. It should also be understood that staple forming pockets (550, 570) in each pair of pockets (550, 570) are interlocking in this configuration. In addition, another radius line ($R_L$) extending outwardly from the center of anvil (500) passes through the region of exit surface (514) of staple forming pocket (510) and through the region of exit surface (534) of staple forming pocket (530). Thus, staple forming pockets (510, 530) overlap along a radial dimension. It should also be understood that staple forming pockets (510, 530) in each pair of pockets (510, 530) are interlocking in this configuration.

In the present example, inner array (502) and outer array (504) are configured similarly, such that the inner-most pocket (510) in each pair of inner pockets (510, 530) is on the left-hand side (in the view of FIG. 7) of the pair of pockets (510, 530); and such that the inner-most pocket (570) in each pair of outer pockets (550, 570) is on the left-hand side (in the view of FIG. 7) of the pair of pockets (550, 570).

Also in the present example, the end of wall (536) associated with staple entry surface (532) includes a bent region (537), which bends slightly inwardly toward the central region of anvil (500). It should be understood that this bent region (537) may be formed in order to maintain a minimum distance between wall (536) and wall (576), thereby maintaining a minimum distance between staple forming pocket (530) and staple forming pocket (570), which may further provide more reliable manufacturing of anvil (600). In addition, bent region (537) may provide different behavior of the second leg of the staple (90) that is formed by staple forming pocket (530). Such different behavior may relate to deflections in anvil (500) and/or a tilt that might result in the first and second legs of a given staple (90) contacting corresponding surfaces (512, 532) at different times during actuation of stapling head assembly (300).

It should also be understood that the presence of bent region (537) provides staple forming pocket (530) with a structural configuration that makes staple forming pocket (530) unique relative to the other staple forming pockets (510, 550, 570). By contrast, the structural configuration of staple forming pocket (510) is identical to the structural configuration of staple forming pocket (570); while the structural configuration of staple forming pocket (550) is the mirrored inverse of the structural configuration of staple forming pockets (510, 570).

In the present example, the spacing between pockets (510, 530) in each pair of pockets (510, 530) is equal to the spacing between pockets (550, 570) in each pair of pockets (550, 570). Thus, staples (90) formed by pockets (510, 530) will have the same crown width as staples formed by pockets (550, 570). In some other versions, however, the spacing between pockets (510, 530) in each pair of pockets (510, 530) is smaller than the spacing between pockets (550, 570) in each pair of pockets (550, 570). In such versions, pockets (550, 570) may be used to form staples (90) having a longer crown width than staples (90) that are formed using pockets (510, 530). As another merely illustrative variation, the spacing between pockets (510, 530) in each pair of pockets (510, 530) may be larger than the spacing between pockets (550, 570) in each pair of pockets (550, 570). In such versions, pockets (550, 570) may be used to form staples (90) having a shorter crown width than staples (90) that are formed using pockets (510, 530). In other words, where at least two annular arrays of staples are formed, staples (90) in one array may have a larger, smaller, or same crown width as staples (90) in another annular array.

As also seen in FIG. 7, staple forming pockets (510, 530) are arranged such that they are not fully centered along a circumferential line ($C_L$) extending along surface (506) at a constant radius from the center of anvil (500). The outermost regions of staple entry surfaces (512, 532) are radially centered along the same circumferential line ($C_L$). However, staple forming pocket (510) is oriented substantially obliquely relative to circumferential line ($C_L$), such that staple exit surface (514) is positioned substantially radially inwardly from circumferential line ($C_L$). By contrast, staple exit surface (534) is positioned substantially along, with a portion position slightly radially outwardly from, circumferential line ($C_L$). In other words, while staple forming pocket (530) is substantially aligned along circumferential line ($C_L$), staple forming pocket (510) is substantially tilted radially inwardly relative to circumferential line ($C_L$), with the outermost regions of staple entry surfaces (512, 532) being radially centered along a circumferential line ($C_L$).

While the views depicted in FIGS. 7-8 only show a portion of the full circumference of anvil (500), it should be understood that the structures depicted in FIGS. 7-8 extend along the full circumference of anvil (500). The views of FIGS. 7-8 are simply being provided as an enlargement to show the structure in further detail, and are not intended to suggest that the depicted structures are only located in a limited angular range along the circumference of anvil (500).

Those of ordinary skill in the art will understand that staples formed by anvil (500) will have a three-dimensional profile, where the legs are angularly offset from a plane passing through a crown of the staple; in addition to being bent generally toward each other. By way of example only, the staples formed using anvil (500) may have an appearance similar to at least some of the staples shown and described in U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. By way of further example only, the staples formed using anvil (500) may have an appearance similar to at least some of the staples shown and described in U.S. patent application Ser. No. 15/350,621, entitled "Staple Forming Pocket Configurations for Circular Surgical Stapler Anvil," filed Nov. 14, 2016, published as U.S. Pub. No. 2018/0132849 on May 17, 2019, now abandoned, the disclosure of which is incorporated by reference herein.

In addition to or in lieu of the foregoing, anvil (400) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

III. Illustrative Stapling Head Assembly

A. Overview

Figure 9:
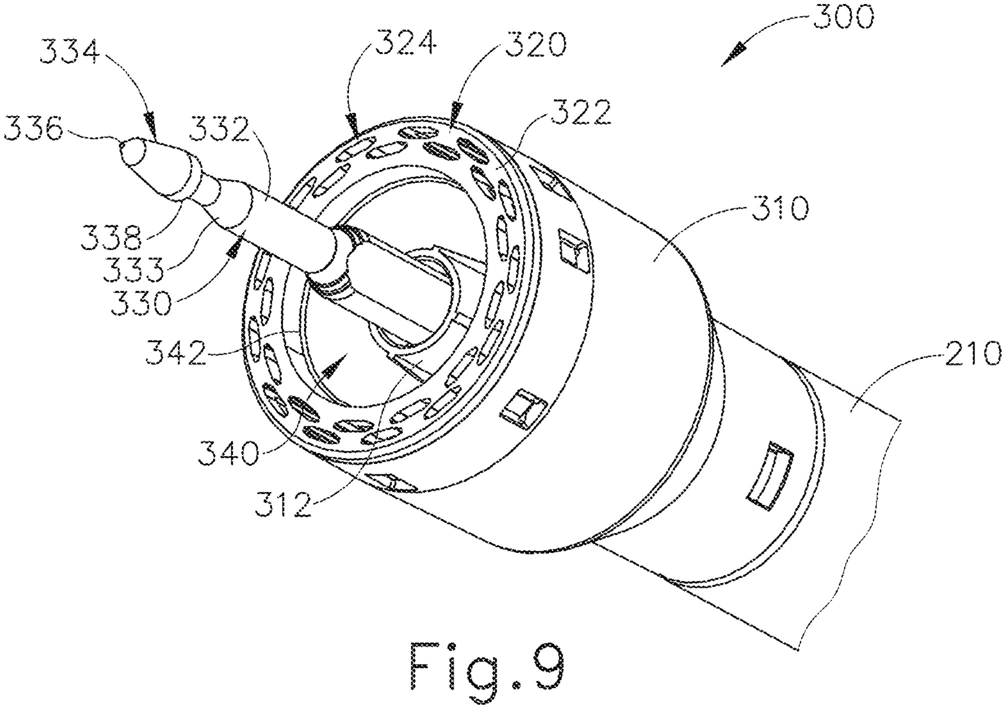
FIG. 9 depicts a perspective view of the stapling head assembly of the circular stapler of FIG. 1.
Figure 10:
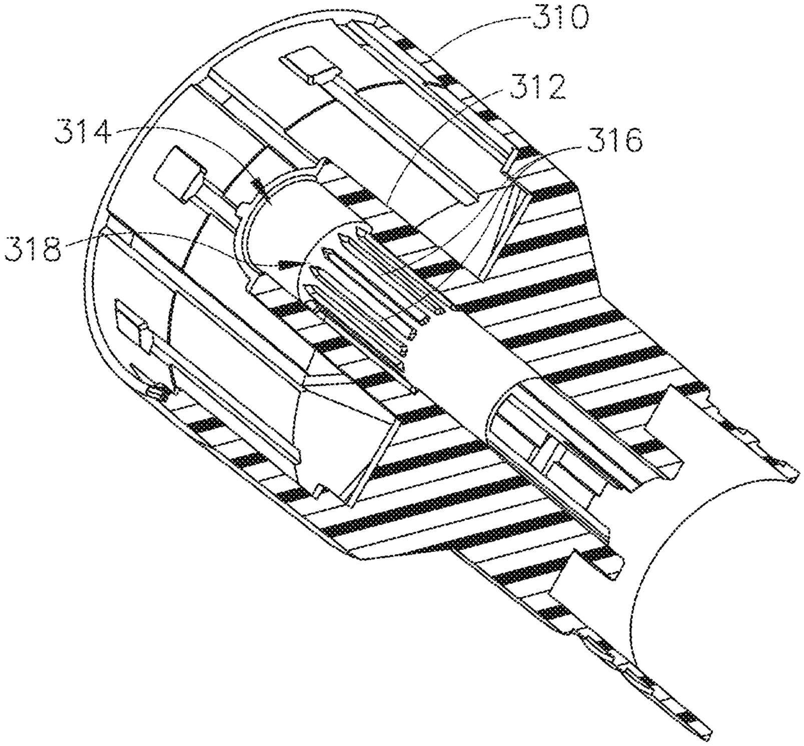
FIG. 10 depicts a perspective cross-sectional view of an inner body member of the stapling head assembly of FIG. 9.
Figure 11:
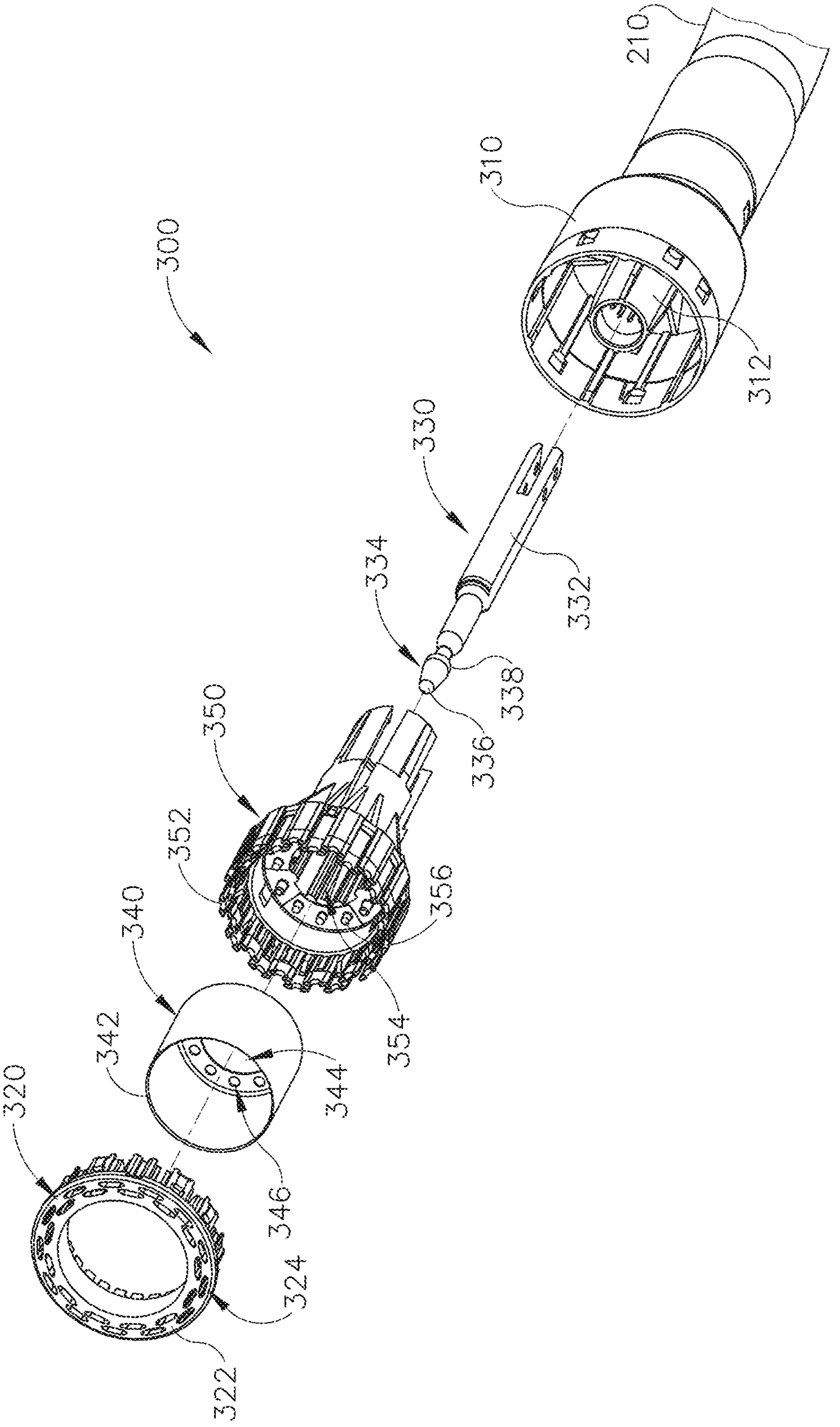
FIG. 11 depicts an exploded perspective view of the stapling head assembly of FIG. 9.

As best seen in FIGS. 9-11, stapling head assembly (300) of the present example is coupled to a distal end of shaft assembly (200) and comprises a body member (310) and a slidable staple driver member (350). Body member (310) includes a distally extending cylindraceous inner core member (312). Body member (310) is fixedly secured to an outer sheath (210) of shaft assembly (200). Body member (310) and outer sheath (210) thus serve together as a mechanical ground for stapling head assembly (300).

As shown in FIG. 10, inner core member (312) of body member (310) defines a bore (314). A plurality of longitudinally extending splines (316) are equidistantly spaced in an angular array within bore (314). The distal ends of splines (316) include lead-in edges (318) that are configured to complement lead-in edges (428) of splines (426) on shank (420) of anvil (400). In particular, after shank (420) is secured to trocar (330) as described in greater detail below, and as anvil (420) is thereafter retracted proximally relative to stapling head assembly (300) as also described in greater detail below, lead-in edges (318, 428) may cooperatively engage each other to drive anvil (400) to rotate relative to trocar (330) to angularly align splines (426) of anvil (400) with the gaps between splines (316) of body member (310). The gaps between splines (316) may be configured to have a width that is substantially equal to the width of splines (426). In this manner, when splines (426) of anvil (400) are positioned within the gaps between splines (316) of body member (310), anvil (400) may achieve a predetermined angular alignment relative to stapling head assembly (300). This predetermined angular alignment may ensure that staple openings (324) of deck member (320) are precisely aligned with corresponding staple forming pockets (414, 510, 530) of anvil (400). Thus, splines (316, 426) are configured to cooperate with each other to ensure that staples ejected through staple openings (324) are accurately driven into corresponding staple forming pockets (414, 510, 530) on a consistent basis, regardless of the angular orientation of anvil (400) relative to stapling head assembly (300) at the time anvil (400) is initially secured to trocar (330).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332)

and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (420). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430).

Staple driver member (350) is operable to actuate longitudinally within body member (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. It should be understood that the arrangement of staple drivers (352) may be modified just like the arrangement of staple forming pockets (414) as described above. Staple driver member (350) also defines a bore (354) that is configured to coaxially receive core member (312) of body member (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of body member (310). An annular array of openings (346) formed in knife member (340) is configured to complement the annular array of studs (356) of staple driver member (350), such that knife member (340) is fixedly secured to staple driver member (350) via studs (356) and openings (346). By way of example only, studs (356) may be heat staked to knife member (340) using techniques known in the art. Other suitable structural relationships between knife member (340) and stapler driver member (350) will be apparent to those of ordinary skill in the art in view of the teachings herein.

A deck member (320) is fixedly secured to body member (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

As best seen in FIG. 9, deck member (320) defines an inner diameter that is just slightly larger than the outer diameter defined by knife member (340). Deck member (320) is thus configured to allow knife member (340) to translate distally to a point where cutting edge (342) is distal to deck surface (322).

B. Illustrative Tissue Gripping Features

Figure 12:
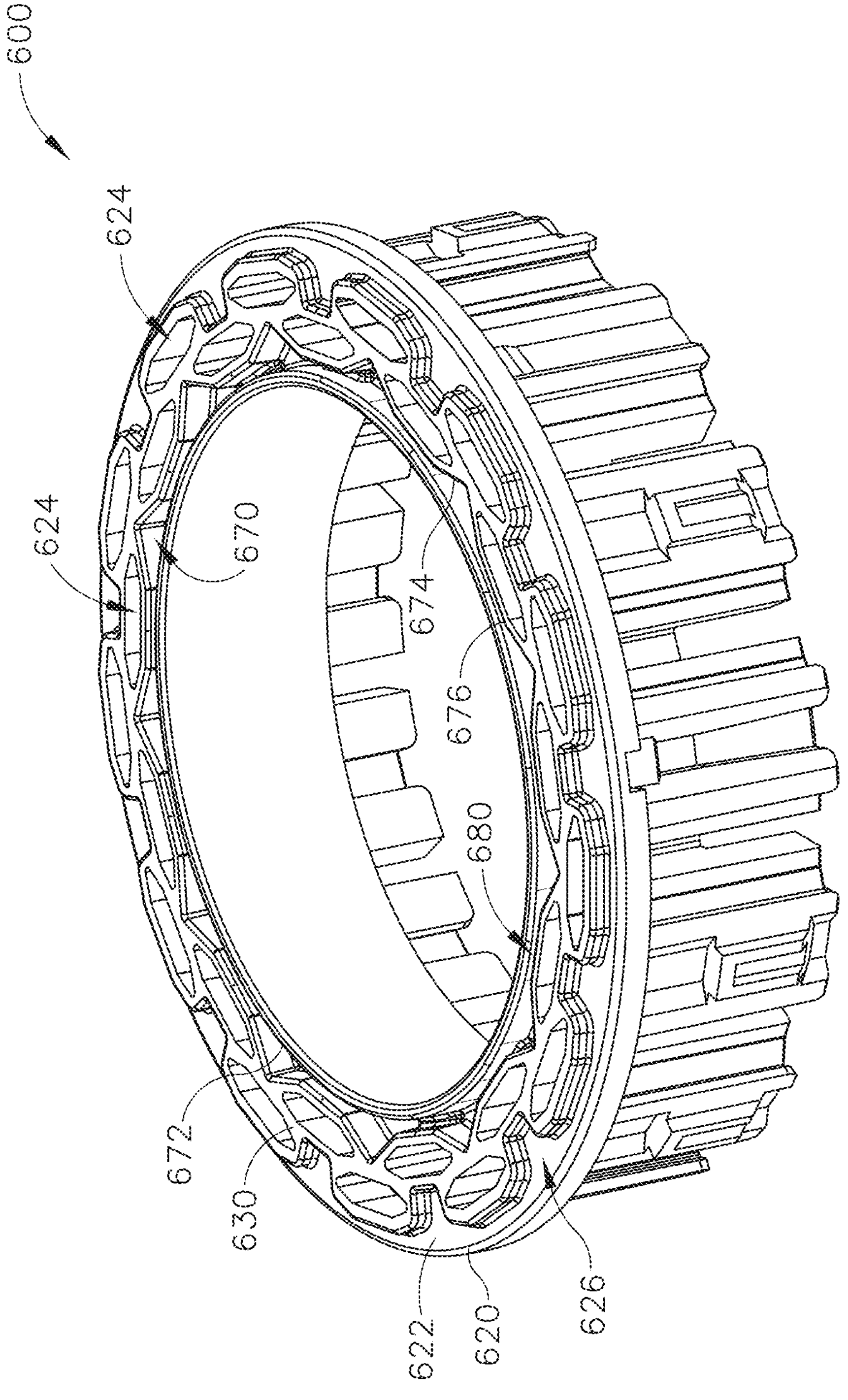
FIG. 12 depicts a perspective view of an illustrative alternative deck member that may be incorporated into the stapling head assembly of FIG. 9.
Figure 13:
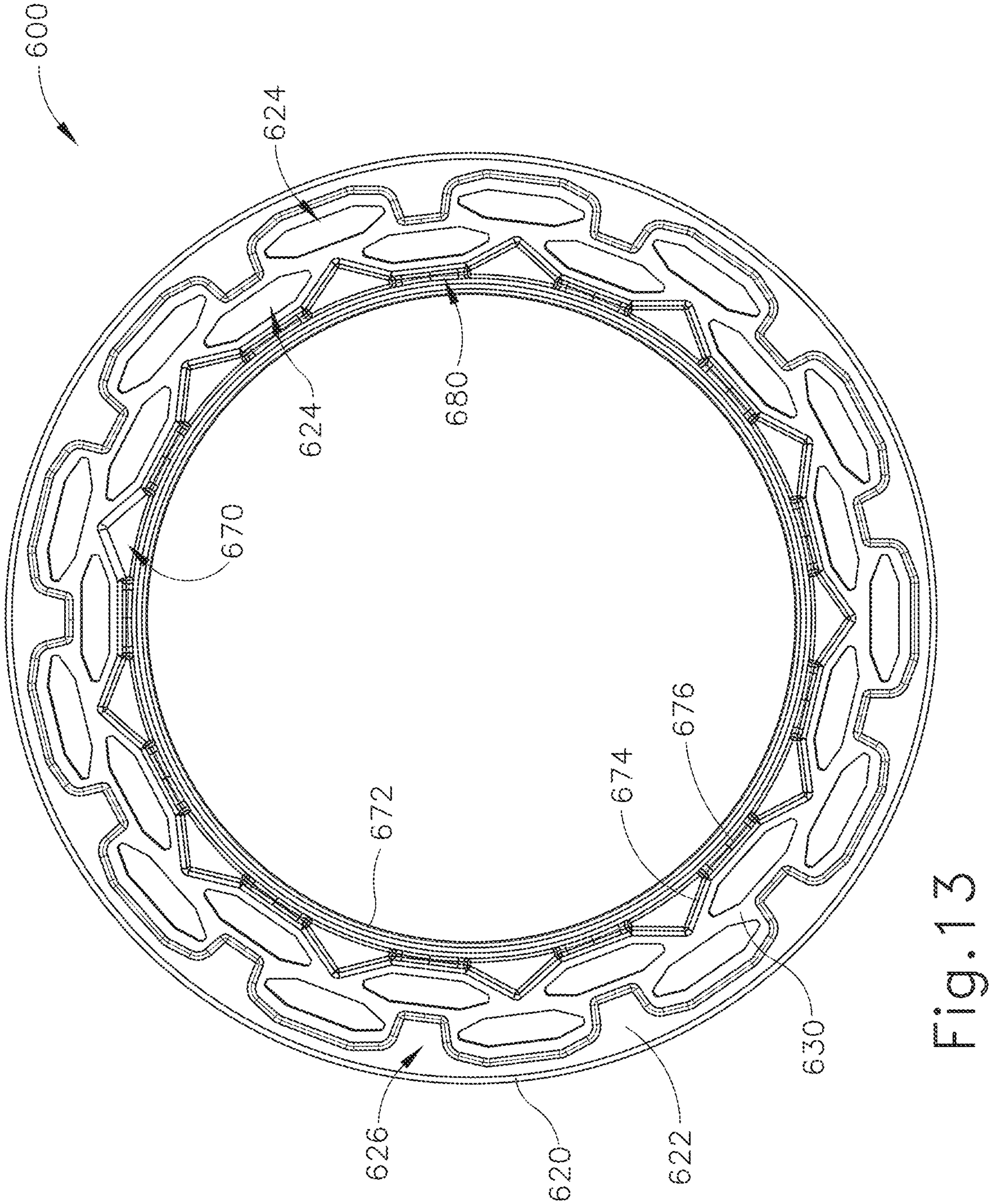
FIG. 13 depicts a top plan view of the deck member of FIG. 12.

It may be desirable to provide a version of stapling head assembly (300) that includes features that enhance gripping of tissue during actuation of stapling head assembly (300), thereby promoting successful tissue cutting and staple deployment, without increasing the risk of damaging the patient's tissue as stapling head assembly (300) slides along the tissue during positioning of stapling head assembly (300). FIGS. 12-13 show an example of a deck member (600) that provides enhanced tissue gripping effects without increasing the risk of tissue damage. Deck member (600) may be readily incorporated into stapling head assembly (300) in place of deck member (320).

Deck member (600) of this example includes a first deck surface (622), a second deck surface (630), and two concentric annular arrays of staple openings (624). Staple openings (624) are arranged to correspond with the arrangement of staple drivers (352) and staple forming pockets (414) described above. Thus, each staple opening (624) is configured to provide a path for a corresponding staple driver (352) to drive a corresponding staple through deck member (600) and into a corresponding staple forming pocket (414) when a stapling head assembly (300) incorporating deck member (600) is actuated. Deck member (600) defines an inner diameter that is just slightly larger than the outer diameter defined by knife member (340). Deck member (600) is thus configured to allow knife member (340) to translate distally to a point where cutting edge (342) is distal to the plane of second deck surface (630).

In the present example, an outer edge (620) spans around the full circumference of deck member (600) with a consistent surface geometry. In the present example, outer edge (620) is configured to prevent outer edge (620) from snagging on tissue. In some versions, outer edge (620) has a curved profile. In some other versions, outer edge (620) has a chamfered profile. Alternatively, outer edge (620) may have any other suitable kind of profile.

Second deck surface (630) is proud relative to first deck surface (622), such that first deck surface (622) is recessed relative to second deck surface (630). As shown, second deck surface (630) fully surrounds each and every staple opening (624), including the inner array of staple openings (624) and the outer array of staple openings (624). However, first deck surface (622) extends inwardly between staple openings (624) of the outer array of staple openings (624), thereby creating gaps (626) in second deck surface (630) between staple openings (624) of the outer array of staple openings (624).

A plurality of recesses (670) are spaced between the staple openings (624) of the inner annular array of staple openings (624). Recesses (670) of the present example are generally shaped like isosceles triangles, with each triangle being defined by a pair of straight walls (674) having equal length and an inner annular wall (672). The vertexes formed by walls (674) are positioned at the radially outermost points of recesses (670). In particular, these vertexes are located at radial positions corresponding to the same circumference at which the angularly outermost points of staple openings (624) are located. In other words, these vertexes of recesses (670) and corresponding points of staple openings (624) are all positioned at the same radial distance along the same circumference in this example. Alternatively, the position and configuration of recesses (670) may have any other suitable relationship with the position and configuration of staple openings (624).

Recesses (670) of the present example are joined together by channels (680) which are defined between inner annular wall (672) and respective opposing annular walls (676). Walls (672, 676) are parallel with each other and are closely positioned relative to each other, such that channels (680) are substantially small in comparison to recesses (670).

Gaps (626), recesses (670), and channels (680) are configured to receive tissue as tissue is being compressed against deck surfaces (622, 630) by anvil (400) as described above. In particular, when anvil (400) is actuated via knob (130) to compress tissue between anvil (400) and deck surfaces (622, 630), portions of the compressed tissue will enter gaps (626), recesses (670), and channels (680). By having some of the tissue enter gaps (626), recesses (670), and channels (680), this may reduce the total pressure that would otherwise be applied to the tissue if the tissue were being compressed against a consistently flat deck surface like deck surface (322). The pressure on tissue is thus concentrated only in the areas where pressure is actually needed-immediately adjacent to staple openings (624). By reducing the total pressure on the tissue, deck member (600) may reduce the risk of the tissue from becoming fractured by over-compression. In addition to reducing the total pressure on tissue, the entry of tissue portions in gaps (626), recesses (670), and channels (680) may provide a grip on the compressed tissue that is greater than the grip that could otherwise be achieved using a consistently flat deck surface like deck surface (322). The enhanced grip of tissue may promote cleaner cutting by knife member (340) and also promote more successful deployment of staples (90) in the tissue. Thus, the presence of gaps (626), recesses (670), and channels (680) may both reduce the risk of over-compression of tissue and promote greater success in cutting and stapling the tissue.

In the present example, gaps (626), recesses (670), and channels (680) all extend to substantially the same depth relative to second deck surface (630). In some other versions, gaps (626), recesses (670), and channels (680) extend to different depths relative to second deck surface (630). For instance, gaps (626) may extend to greater depths than recesses (670) relative to second deck surface (630) or vice versa. It should also be understood that gaps (626) may alternate depths relative to second deck surface (630), such that gaps (626) alternate between a relatively shallow gap (626) and a relatively deep gap (626) along at least a portion of the angular range of deck member (600). Similarly, recesses (670) may alternate depths relative to second deck surface (630), such that recesses (670) alternate between a relatively shallow recess (670) and a relatively deep recess (670) along at least a portion of the angular range of deck member (600). As yet another merely illustrative variation, the depth of a given gap (626) or recess (670) may vary within that particular gap (626) or recess (670). For instance, the radially innermost region of a given gap (626) may be deeper or shallower than the radially outermost region of that same gap (626). Similarly, the region of each recess (670) near the vertex may be deeper or shallower than the region of each recess (670) near inner annular wall (672). Other suitable variations that may be provided in the depth of gaps (626), recesses (670), and/or channels (680) relative to second deck surface (630) will be apparent to those of ordinary skill in the art in view of the teachings herein.

Inner annular wall (672) extends consistently along the full circumference of deck member (600). In particular, the height of the uppermost edge of inner annular wall (672) is consistent along the full circumference of deck member (600). The uppermost edge of inner annular wall (672) is thus configured to provide consistent pressure against the adjacent annular region of tissue as the tissue is being compressed against deck member (600) by anvil (400). This application of consistent pressure against the adjacent annular region of tissue may further assist in clean cutting of the tissue by knife member (340), particularly since knife member (340) will be severing the tissue right next to the uppermost edge of inner annular wall (672). In the present example, the uppermost edge of inner annular wall (672) is substantially flush with second deck surface (630). In some other variations, the uppermost edge of inner annular wall (672) is proud or raised relative to second deck surface (630). In still other variations, the uppermost edge of inner annular wall (672) is recessed or lower relative to second deck surface (630).

C. Illustrative Anvil Coupling Detection

In some versions of instrument (10) it may desirable to provide instrument (10) with features that are configured to indicate proper and/or improper attachment of anvil (400) to trocar (330) of stapling head assembly (300). For instance, if anvil (400) is not properly attached to trocar (330), an operator may receive audible and/or tactile feedback indicating improper attachment. Additionally, if anvil (400) is properly attached to trocar (330), an operator may receive audible, tactile, and/or visible feedback indicating proper attachment. In addition or in the alternative, features may be configured to prevent firing of stapling head assembly (300) unless anvil (400) is properly attached to trocar (300). For instance, if anvil (400) is not properly attached to trocar (330), stapling head assembly (300) may be prevented from firing. If anvil (400) is properly attached to trocar (330), firing of stapling head assembly (300) may be enabled. Various examples of such features will be described in greater detail below; while other examples will be apparent to those of ordinary skill in the art in view of the teachings herein. Moreover, the following teachings may be applied to devices that are used in various other contexts.

Figure 14B:
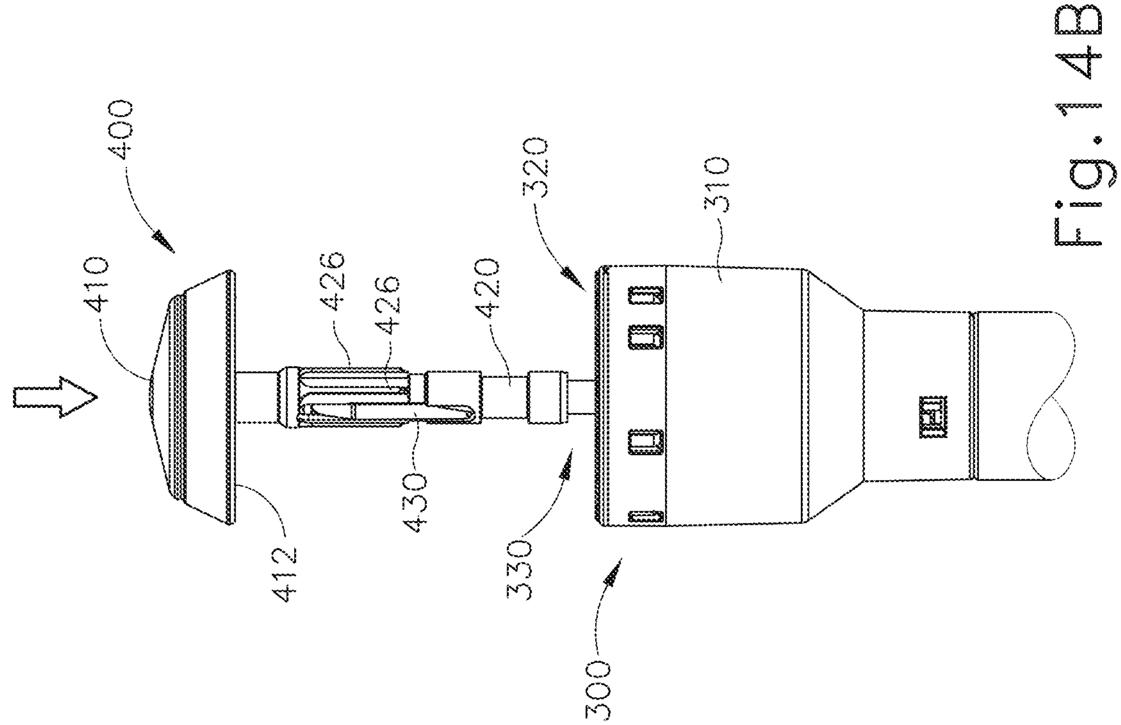
FIG. 14B shows a side elevational view of the anvil of FIG. 3 at a second longitudinal position in relation to the stapling head assembly of FIG. 9.
Figure 14A:
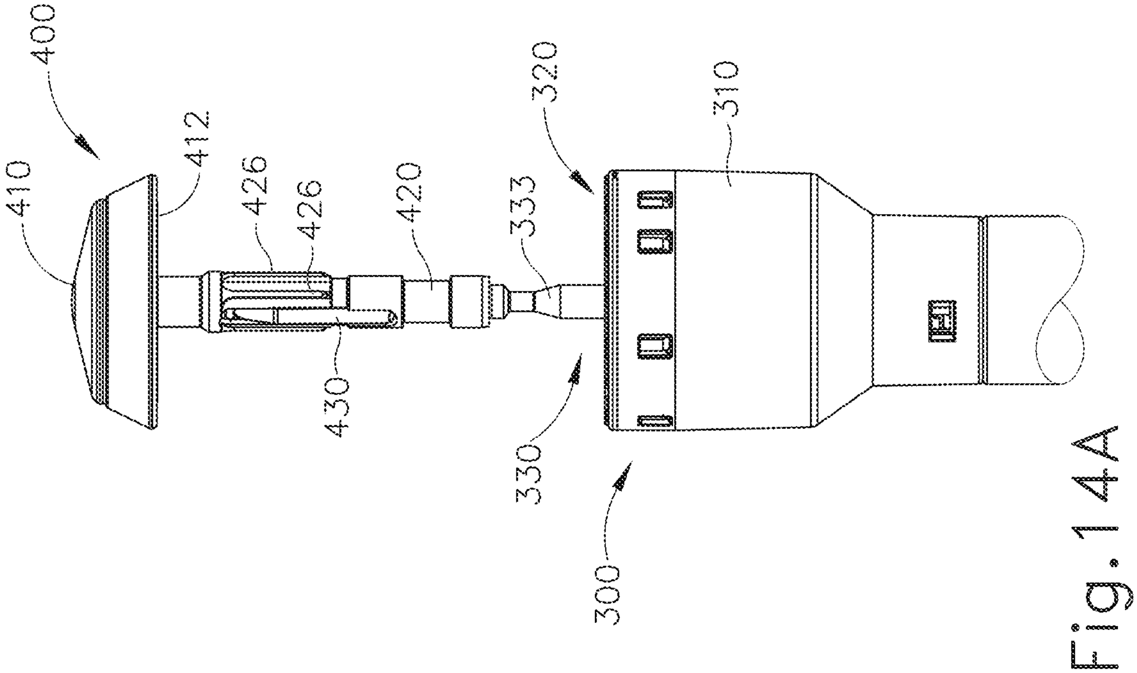
FIG. 14A shows a side elevational view of the anvil of FIG. 3 at a first longitudinal position in relation to the stapling head assembly of FIG. 9.

In the example shown in FIGS. 14A-14B, trocar (330) includes a colored region (333) that is longitudinally positioned at a location where colored region (333) is exposed before shank (420) is fully seated on trocar (330) (FIG. 14A); and covered when shank (420) is fully seated on trocar (330) (FIG. 14B). Colored region (333) may be colored using a color (e.g., orange) that is easily visible in relation to adjacent regions of trocar (330) and shank (420). When coupling shank (420) with trocar (330), the operator may observe colored region (333) to ensure that the entire colored region (333) is obscured by shank (420) before attempting to retract the combination of trocar (330) and anvil (400) relative to stapling head assembly (300). If the operator continues to see even a portion of colored region (333), the operator may continue pressing anvil (400) onto trocar (330) until colored region (333) is completely obscured by shank (420).

Even when trocar (330) includes a visual feedback feature such as colored region (333) to assist the operator with proper seating of anvil (400) on trocar (330), it may still be desirable to include a sensor feature that is operable to detect whether anvil (400) is properly seated on trocar (330). To that end, FIGS. 15A-16B depict an illustrative switch assembly (2600) that is incorporated into stapling head assembly (300) in the present example. Switch assembly (2600) includes a dome switch (2610) and a resilient actuator spring (2602). Actuator spring (2602) is secured within a cavity (2606) formed within body member (310). Dome switch (2610) is positioned between a pair of flanges (2612, 2614) of actuator spring (2602) such that movement of flange (2612) toward flange (2614) will actuate dome switch (2610).

When anvil (400) is properly secured to trocar (330) and is retracted proximally as described herein, anvil (400) causes movement of flange (2612) toward flange (2614) so as to actuate dome switch (2610). Actuation of dome switch (2610) may provide audible, tactile, and/or visible feedback to an operator indicating proper attachment. Various suitable features that may be used to provide such a response to actuation of dome switch (2610) will be apparent to those of ordinary skill in the art in view of the teachings herein. In addition, in the present example actuation of dome switch (2610) may enables firing of stapling head assembly (300). In other words, unless dome switch (2610) has been actuated, stapling head assembly (300) may not be fired in the present example.

Figure 15A:
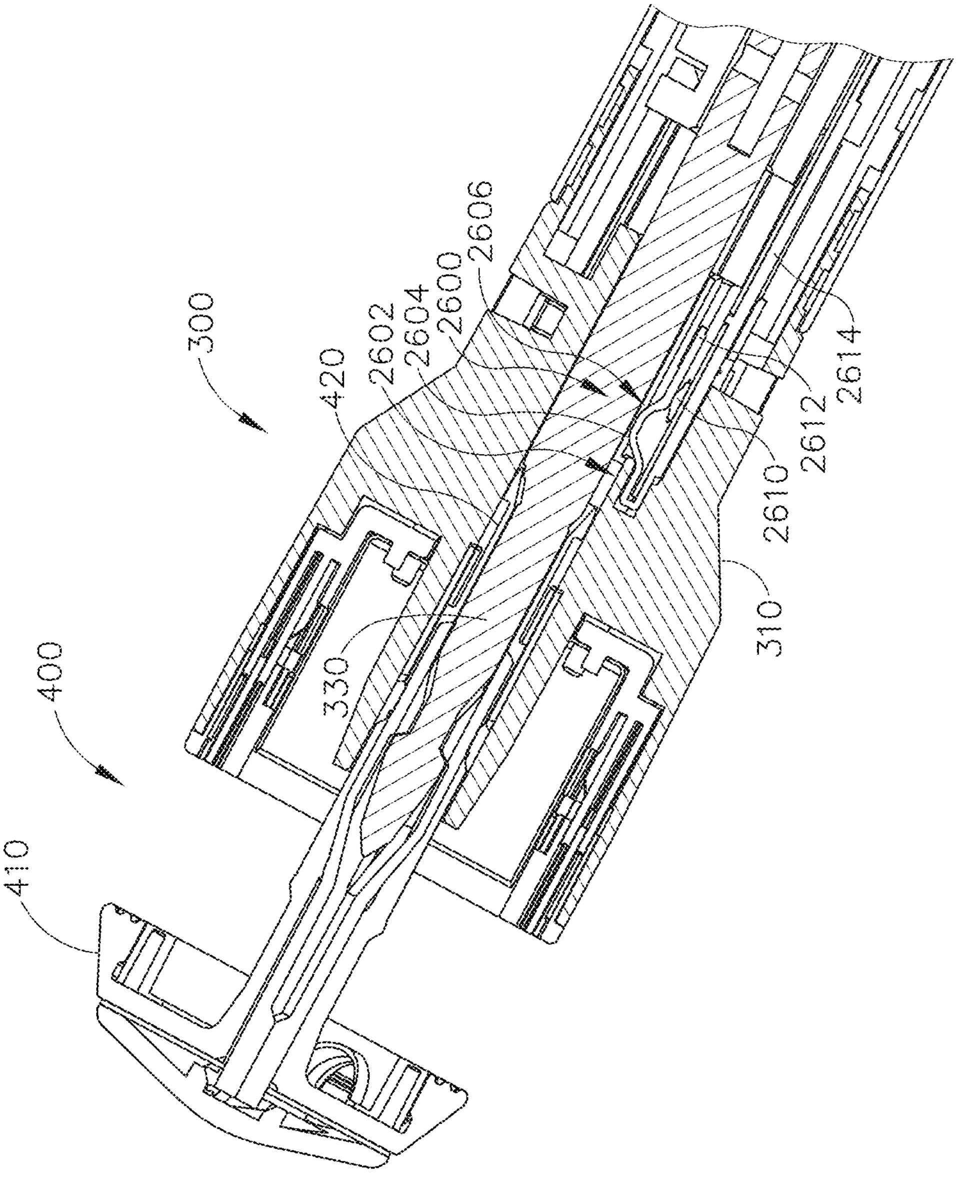
FIG. 15A depicts a cross-sectional side view of the distal end of the circular stapler of FIG. 1, with a contact switch of the circular stapler in an open state.
Figure 15B:
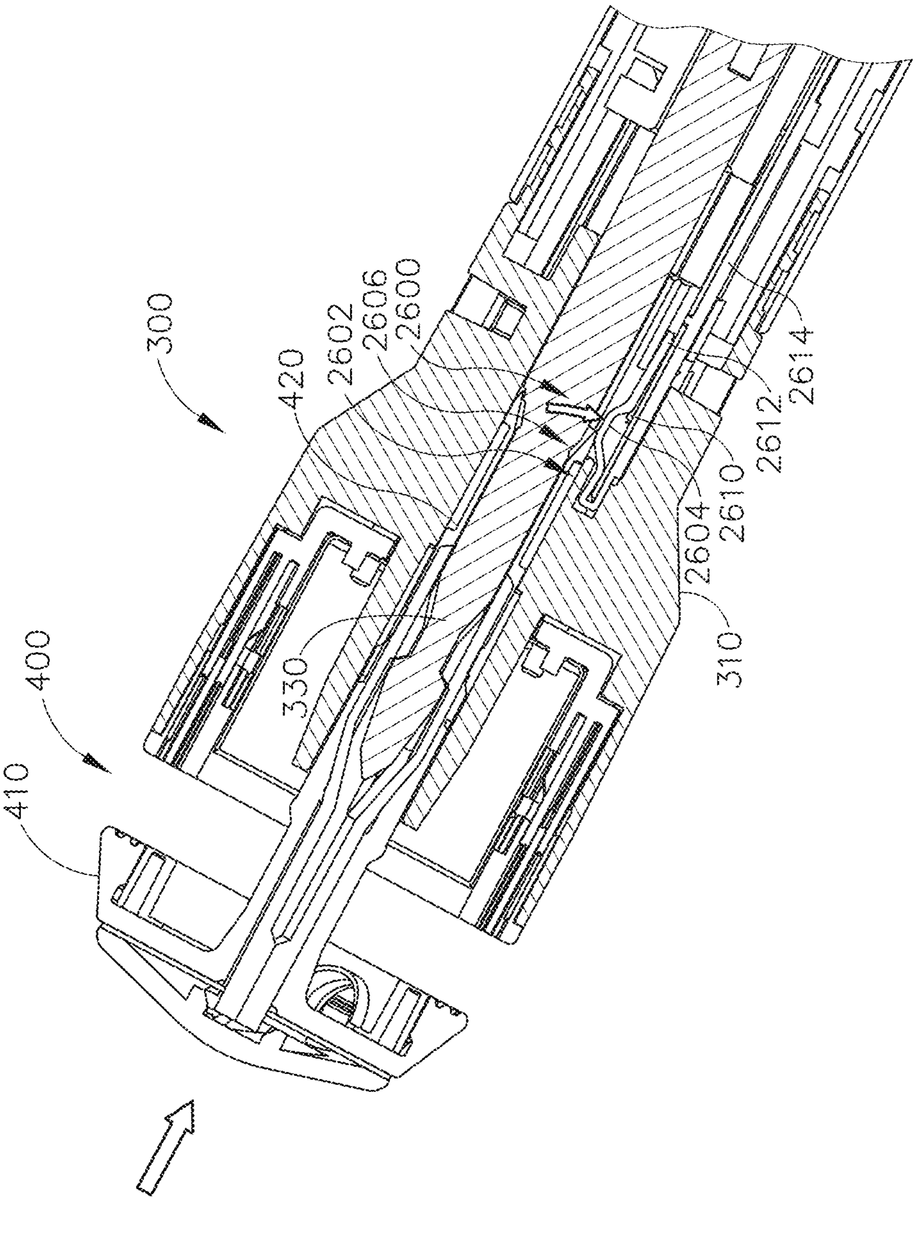
FIG. 15B depicts a cross-sectional side view of the distal end of the circular stapler of FIG. 1, with the contact switch of FIG. 15A moved into a closed state by proximal translation of a trocar and an anvil of the circular stapler.
Figure 16A:
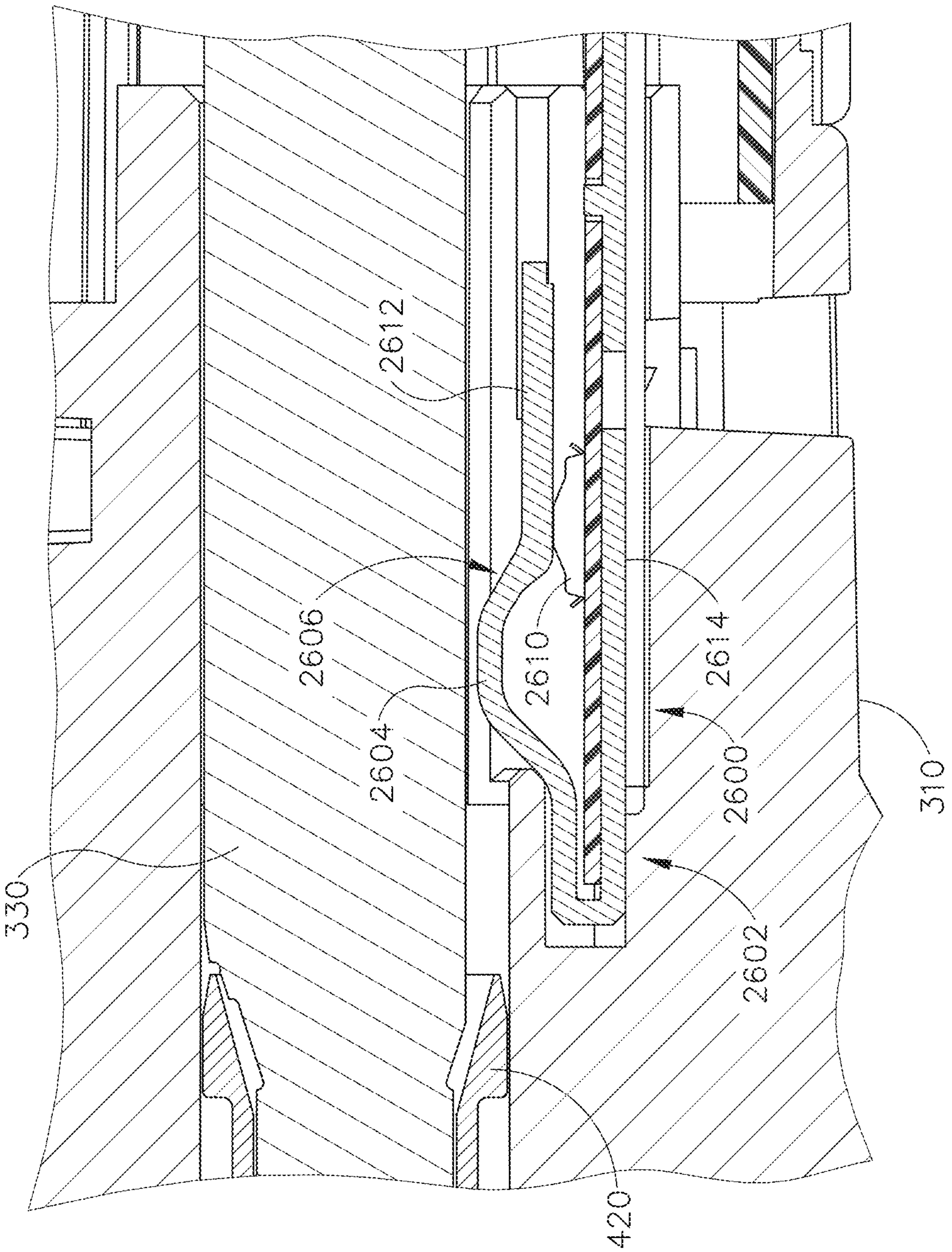
FIG. 16A depicts an enlarged cross-sectional side view of the contact switch of FIG. 15A in the open state of FIG. 15A.
Figure 16B:
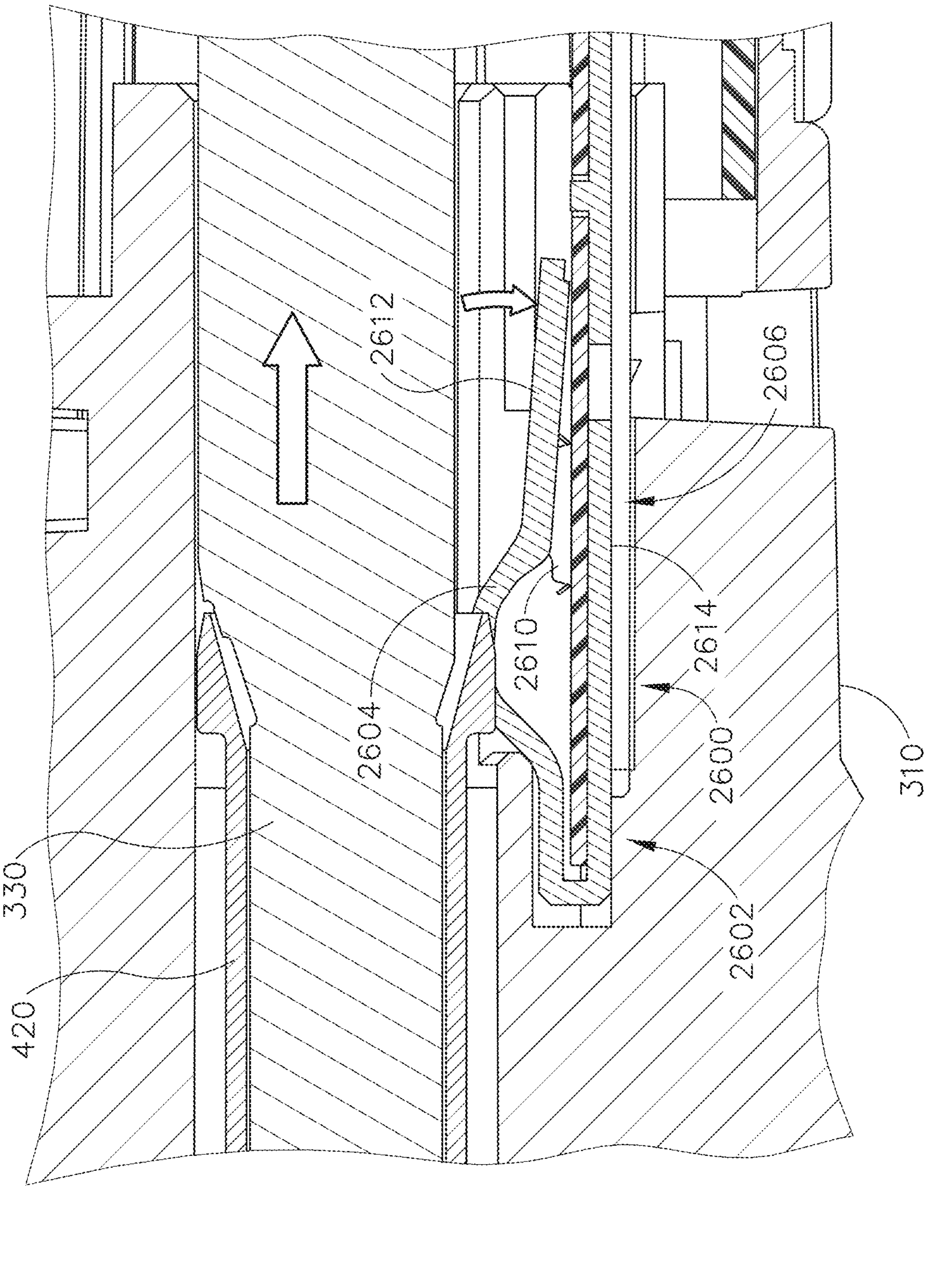
FIG. 16B depicts an enlarged cross-sectional side view of the contact switch of FIG. 15A moved into the closed state of FIG. 15B by proximal translation of the trocar and the anvil of the circular stapler.

After anvil (400) is secured to trocar (330), the operator then rotates knob (130) to cause trocar (330) and anvil (400) to retract proximally as described above. When trocar (330) and anvil (400) are properly secured to one another, the proximal retraction of trocar (330) and anvil (400) compresses the tissue of tubular anatomical structures (20, 40) between surfaces (412, 322) of anvil (400) and stapling head assembly (300) as described herein. When trocar (330) and anvil (400) are not properly secured to one another, trocar (330) is retracted proximally without anvil (400), such that the tissue of tubular anatomical structures (20, 40) remains uncompressed. When trocar (330) and anvil (400) are properly secured to one another, as trocar (330) and anvil (400) are retracted proximally, a proximal end of shank (420) of anvil (400) engages a raised portion (2604) of flange (2612) of actuator spring (2602) and thereby drives flange (2612) toward flange (2614), thereby actuating dome switch (2610) as shown in FIGS. 15B and 16B.

In the present example, dome switch (2610) is not actuated immediately upon proper seating of shank (420) on trocar (330). Instead, trocar (330) and anvil (400) have to be retracted proximally relative to stapling head assembly (300) by at least some distance before dome switch (2610) is actuated. In the present example, dome switch (2610) is actuated before anvil (400) reaches the "green zone" as described herein. In some other variations, dome switch (2610) is not actuated until after anvil (400) reaches the distal-most boundary of the "green zone" as described herein.

As mentioned above, the actuation of dome switch (2610) may provide audible, tactile, and/or visible feedback to an operator indicating proper attachment. Moreover, such actuation of dome switch (2610) enables firing of stapling head assembly (300). In other words, unless dome switch (2610) has been actuated, stapling head assembly (300) may not be fired. An illustrative way in which dome switch (2610) may be integrated into a control circuit (2700) will be described in greater detail below with reference to FIG. 60.

Other examples will be apparent to those of ordinary skill in the art in view of the teachings herein.

In addition to or in lieu of the foregoing, stapling head assembly (300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

IV. Illustrative Drive Assemblies

Figure 17:
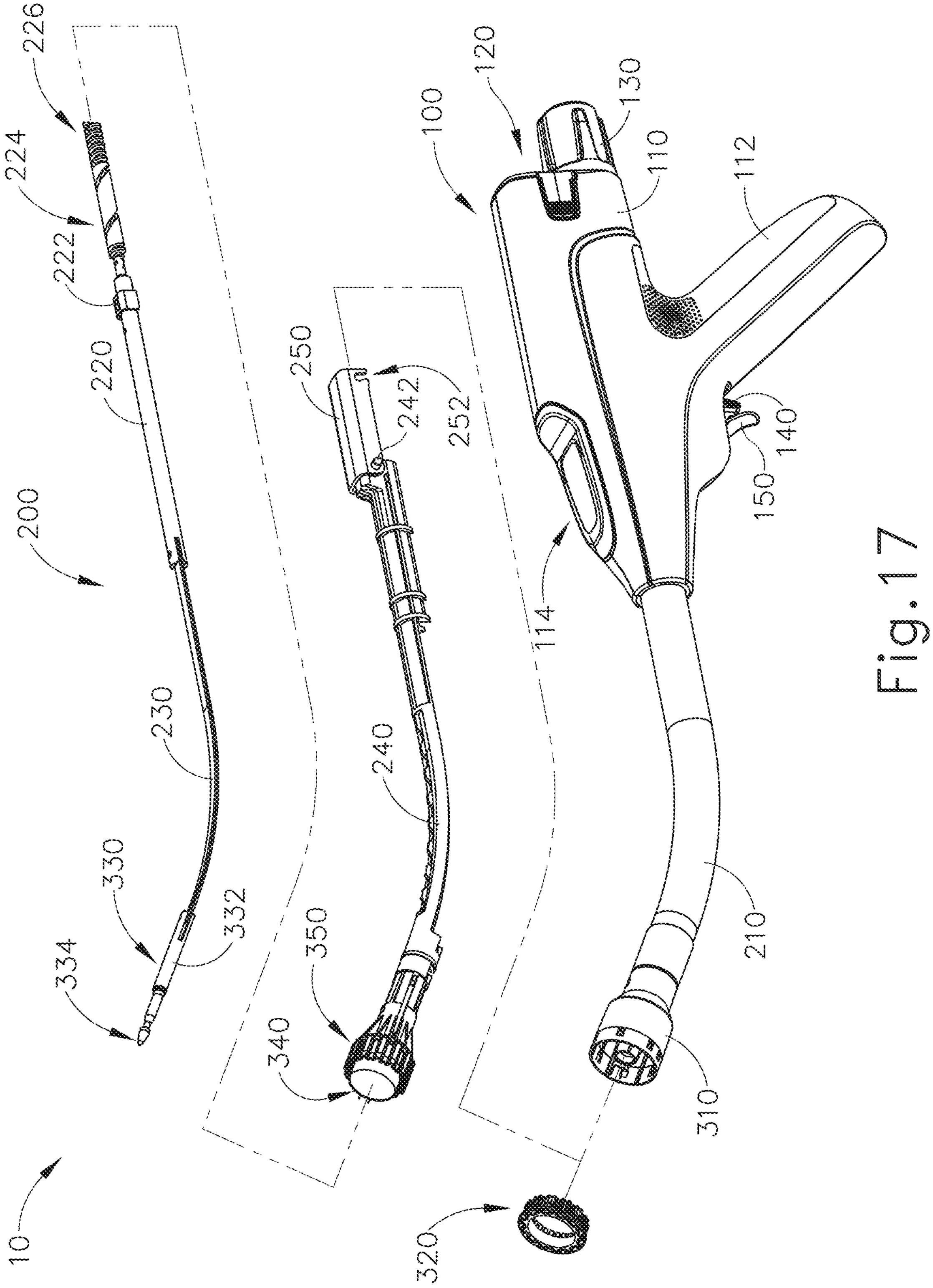
FIG. 17 depicts an exploded perspective view of the circular stapler of FIG. 1, with portions of the shaft assembly shown separately from each other.

FIG. 17 shows various components of shaft assembly (200), which couples components of stapling head assembly (300) with components of handle assembly (100). In particular, and as noted above, shaft assembly (200) includes an outer sheath (210) that extends between handle assembly (100) and body member (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226). Details regarding the movement of trocar actuation rod (220) will be described in greater detail below.

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350). Details regarding the movement of drive bracket (250) will be described in greater detail below.

While not shown in FIG. 17, it should be understood that shaft assembly (200) may further include one or more spacer elements within outer sheath (210). Such spacer elements may be configured to support trocar actuation band assembly (230) and/or stapling head assembly driver (240) as trocar actuation band assembly (230) and/or stapling head assembly driver (240) translate through outer sheath (210). For instance, such spacer elements may prevent trocar actuation band assembly (230) and/or stapling head assembly driver (240) from buckling as trocar actuation band assembly (230) and/or stapling head assembly driver (240) translate through outer sheath (210). Various suitable forms that such spacer elements may take will be apparent to those of ordinary skill in the art in view of the teachings herein.

Figure 18:
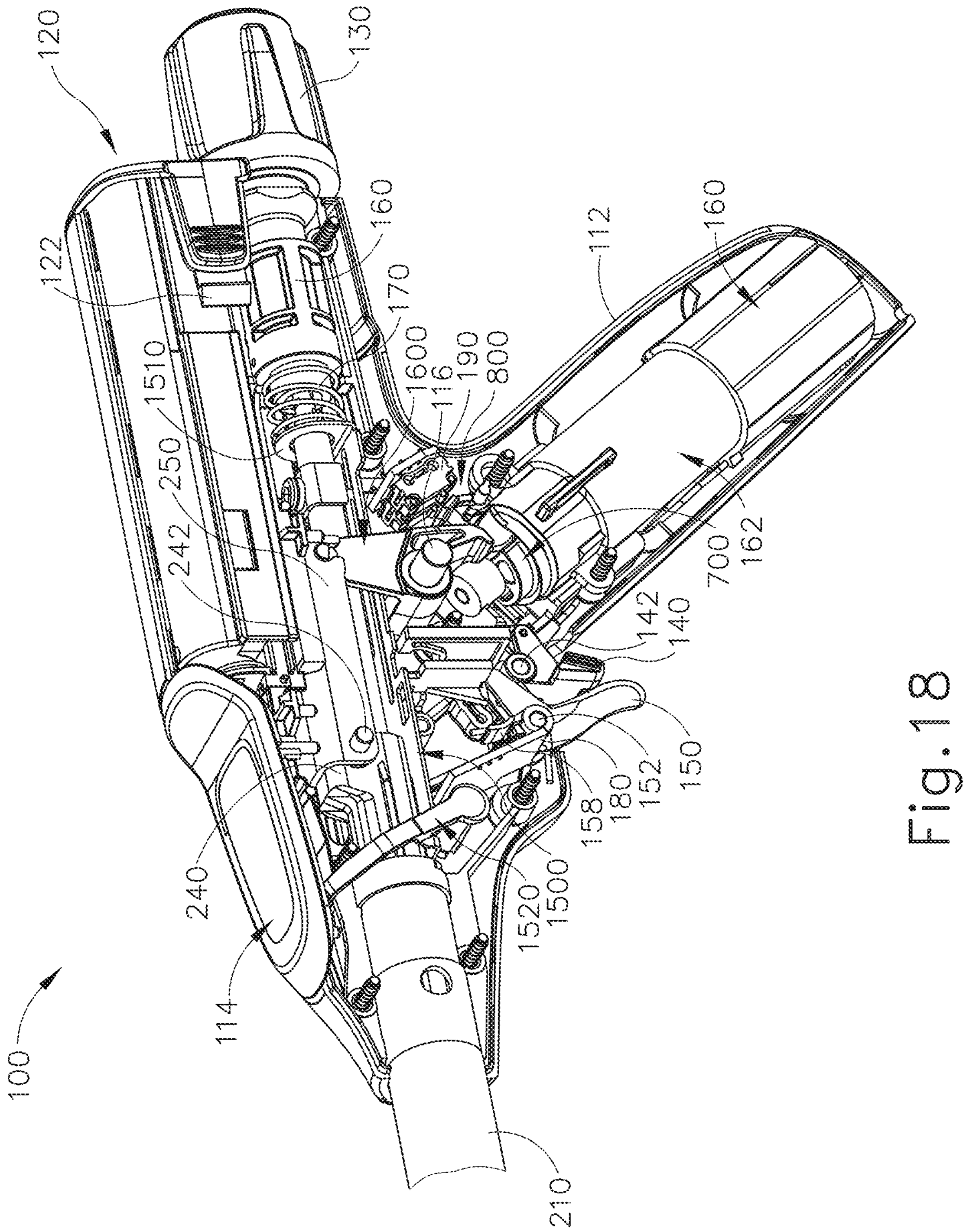
FIG. 18 depicts a perspective view of the handle assembly of the circular stapler of FIG. 1, with a housing half omitted to reveal internal components of the handle assembly.
Figure 19:
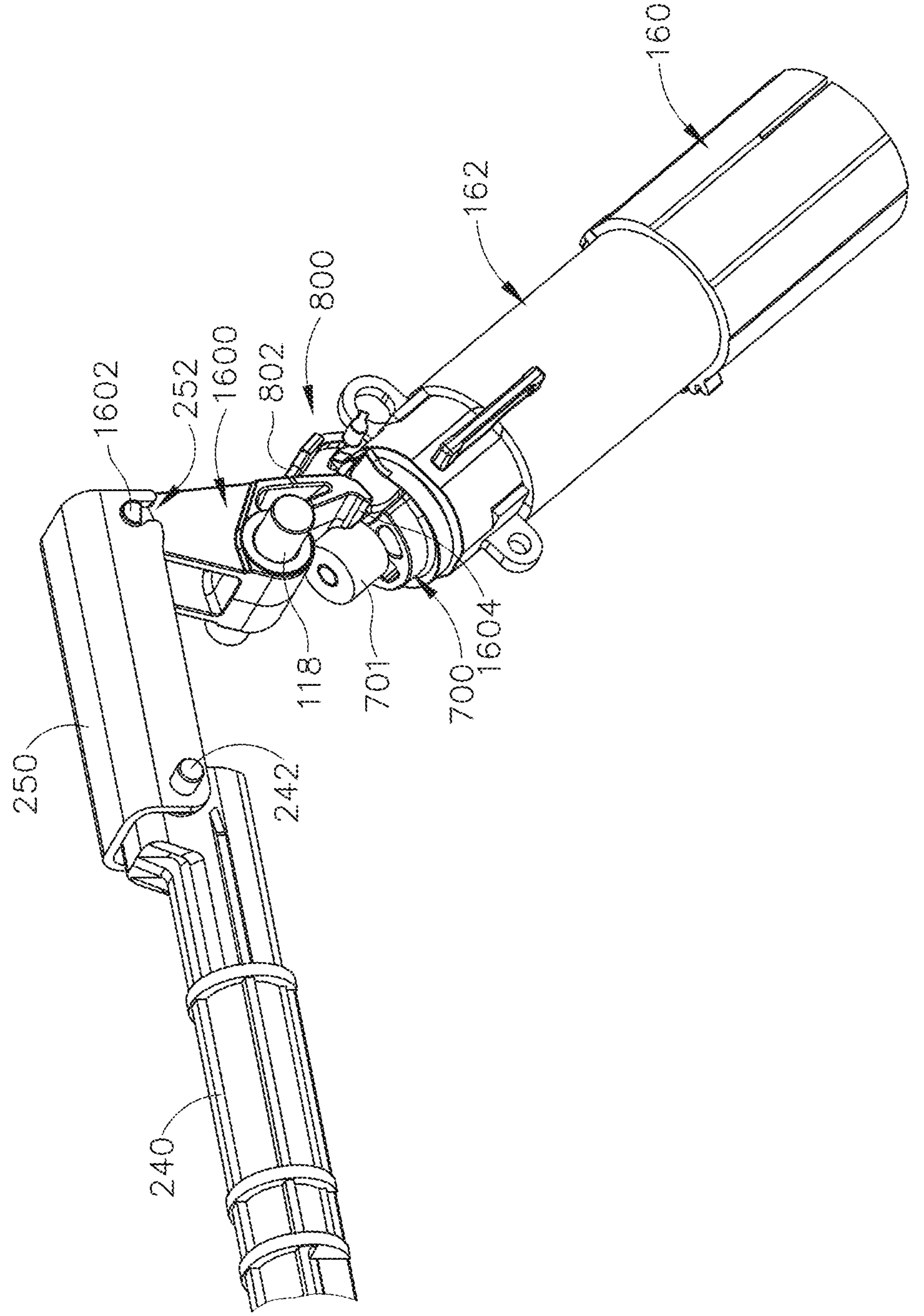
FIG. 19 depicts a perspective view of a stapling head actuation assembly of the circular stapler of FIG. 1.

As shown in FIG. 18, handle assembly (100) includes several components that are operable to actuate anvil (400) and stapling head assembly (300). Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

A. Illustrative Anvil Actuation Assembly

Knob (130) protrudes proximally from casing (110) of handle assembly and is rotatable relative to casing (110). As shown in FIG. 9, a nut (160) is secured to the distal end of knob (130). In the present example, nut (160) is fixedly secured to the distal end of knob (130) such that nut (160) will rotate unitarily with knob (130). Nut (160) and knob (130) are configured to cooperate with trocar actuation rod (220) to thereby translate trocar actuation rod (220) longitudinally relative to casing (110) in response to rotation of nut (160) and knob (130) relative to casing (110). As noted above, trocar (330) will translate longitudinally relative to outer sheath (210) in response to translation of trocar actuation rod (220) relative to outer sheath (210) and casing (110).

The proximal portion of trocar actuation rod (220) is positioned within handle assembly (100) to engage nut (160) and knob (130). In particular, trocar actuation rod (220) is positioned within handle assembly (100) such that coarse helical threading (224) will selectively engage a thread engagement feature (not shown) within the interior of nut (160); and such that fine helical threading (226) will selectively engage a thread engagement feature (not shown) within the interior of knob (130). In some versions, the thread engagement feature of nut (160) comprises an inwardly directed tab; while the thread engagement feature of knob (130) comprises a helical threading. Other suitable forms that such thread engagement features may take will be apparent to those of ordinary skill in the art in view of the teachings herein.

In the present example, when nut (160) and knob (130) are rotated relative to casing (110), trocar actuation rod (220) travels proximally through a first range of longitudinal motion where coarse helical threading (224) is engaged with nut (160) to provide a relatively rapid rate of translation. Fine helical threading (226) is not engaged with knob (130) during this range of motion. When nut (160) and knob (130) are further rotated relative to casing (110) after trocar actuation rod (220) completes the first range of motion, trocar actuation rod (220) will continue to travel proximally through a second range of longitudinal motion where fine helical threading (226) is engaged with knob (130) to provide a relatively slow rate of translation. Thus, trocar actuation rod (220) will translate proximally through a sequence of rapid translation followed by slow translation, based on engagement between coarse helical threading (224) and nut (160) followed by engagement between fine helical threading (226) and knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance (d) between opposing surfaces (412, 322) of anvil (400) and stapling head assembly (300) until a suitable gap distance (d) has been achieved as shown in FIG. 27C and as described in greater detail below.

B. Illustrative Stapling Head Actuation Assembly

FIGS. 19-26D show various components that are operable to actuate stapling head assembly (300). These components include motor (160), a gearbox (162), a rotary cam member (700), a cam follower (1600), drive bracket (250) and stapling head assembly driver (240). Gearbox (162) is coupled with a drive shaft of motor (160) and is further coupled with cam member (700). Activation of motor (160) thus causes rotation of cam member (700) via gearbox (162). By way of example only, gearbox (162) may comprise a multi-stage planetary gearbox. Various suitable configurations that may be used for gearbox (162) will be apparent to those of ordinary skill in the art in view of the teachings herein. Cam member (700) is configured to interact with cam follower (160) to pivot cam follower (160) in two angular directions about a pin (118) as will be described in greater detail below. Pin (118) is coupled with a chassis (e.g., chassis (3690) described below), which is located within casing (110). A bushing (701) provides rotary support to cam member (700) relative to the chassis in casing (110).

Figure 20:
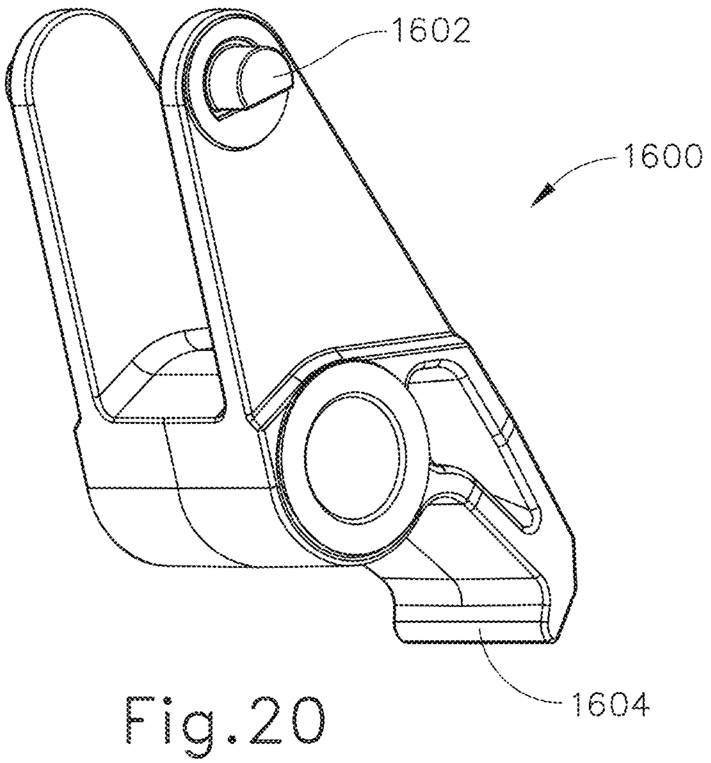
FIG. 20 depicts a perspective view of a cam follower of the stapling head actuation assembly of FIG. 19.
Figure 21:
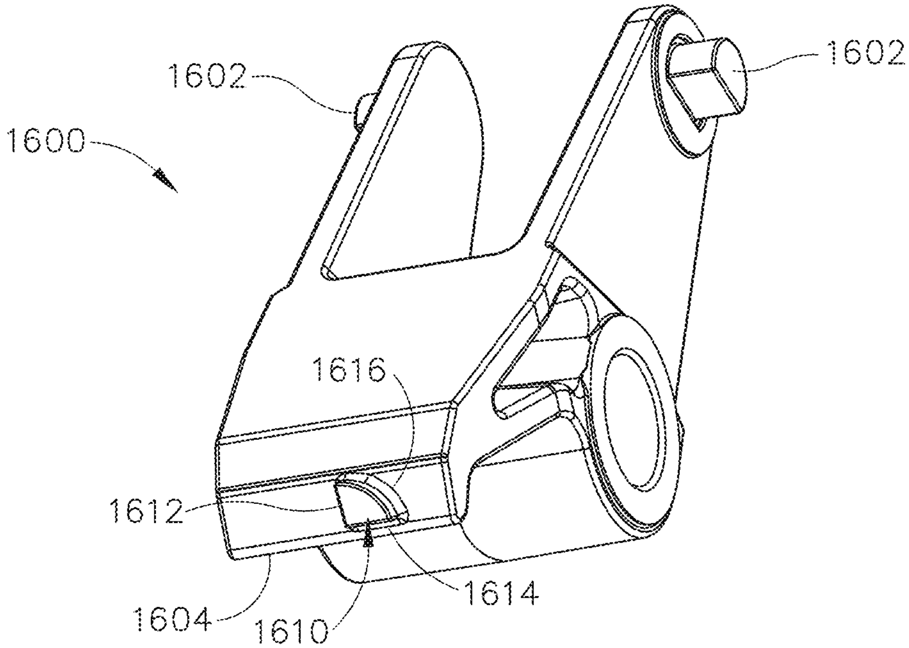
FIG. 21 depicts another perspective view of the cam follower of FIG. 20.

Cam follower (1600) is pivotably coupled with drive bracket (250) via a pair of integral pins (1602), which are received in complementary notches (252) of drive bracket (250). As shown in FIGS. 20-21, cam follower (1600) includes a first bearing feature (1604) and a second bearing feature (1610). First bearing feature (1604) consists of a rounded, horizontally extending surface. Second bearing feature (1610) is shaped like a quarter-pie defined by a straight vertical surface (1612), a horizontally extending surface (1614), and a curved surface (1616). Second bearing feature (1610) projects proximally relative to first bearing feature (1604).

Figure 22:
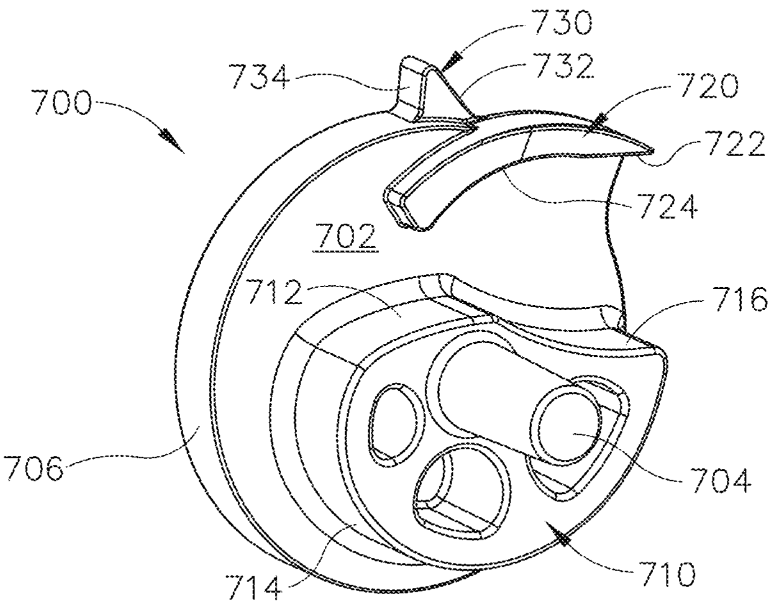
FIG. 22 depicts a perspective view of a rotary cam of the stapling head actuation assembly of FIG. 19.
Figure 23:
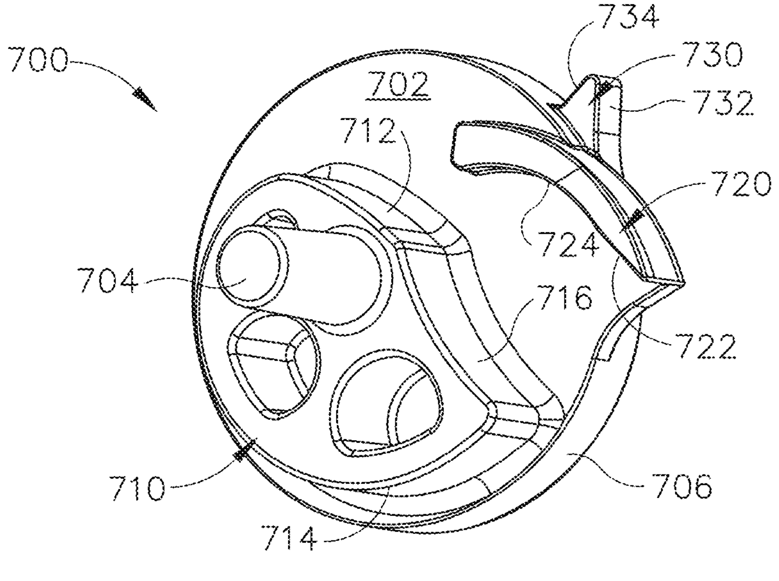
FIG. 23 depicts another perspective view of the rotary cam of FIG. 22.

FIGS. 22-23 show cam member (700) in greater detail. Cam member (700) comprises a distal face (702), a distally projecting post (704), and an outer circumferential surface (706). A first cam feature (710) and a second cam feature (720) project distally from distal face (702). Post (704) engages bushing (701). First cam feature (710) comprises a first surface region (712), a second surface region (714), and a third surface region (716). First surface region (712) is convexly defined by a relatively large radius of curvature, such that first surface region (712) is nearly flat. Second surface region (714) is convexly defined by a progressively increasing radius of curvature. Third surface region (716) is concavely defined by a relatively large radius of curvature.

In addition to projecting distally from distal face (702), second cam feature (720) projects outwardly from outer circumferential surface (706). Second cam feature (720) includes a first surface region (722) and a second surface region (724). First surface region (722) is substantially flat while second surface region (724) is concavely curved. The origin of the radius of curvature for each curved surface region (712, 714, 716, 724) is offset from the center of post (704).

Figure 24A:
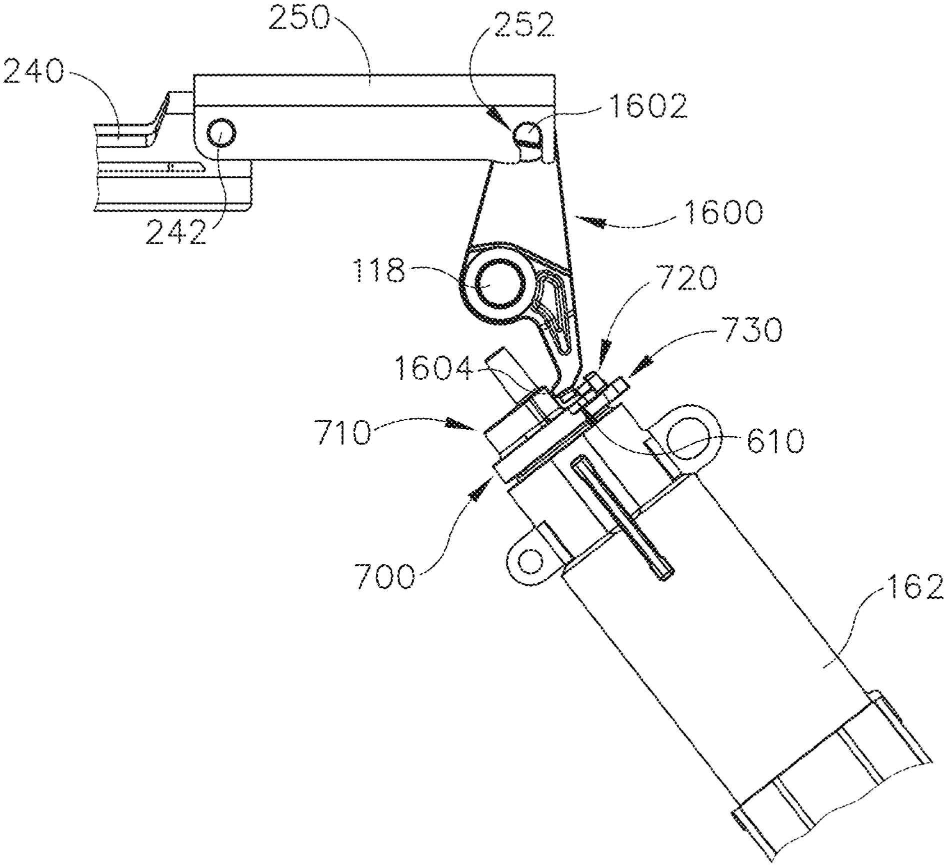
FIG. 24A depicts a side elevational view of the stapling head actuation assembly of FIG. 19, with the rotary cam in a first angular position and the cam follower in a first pivotal position.
Figure 24B:
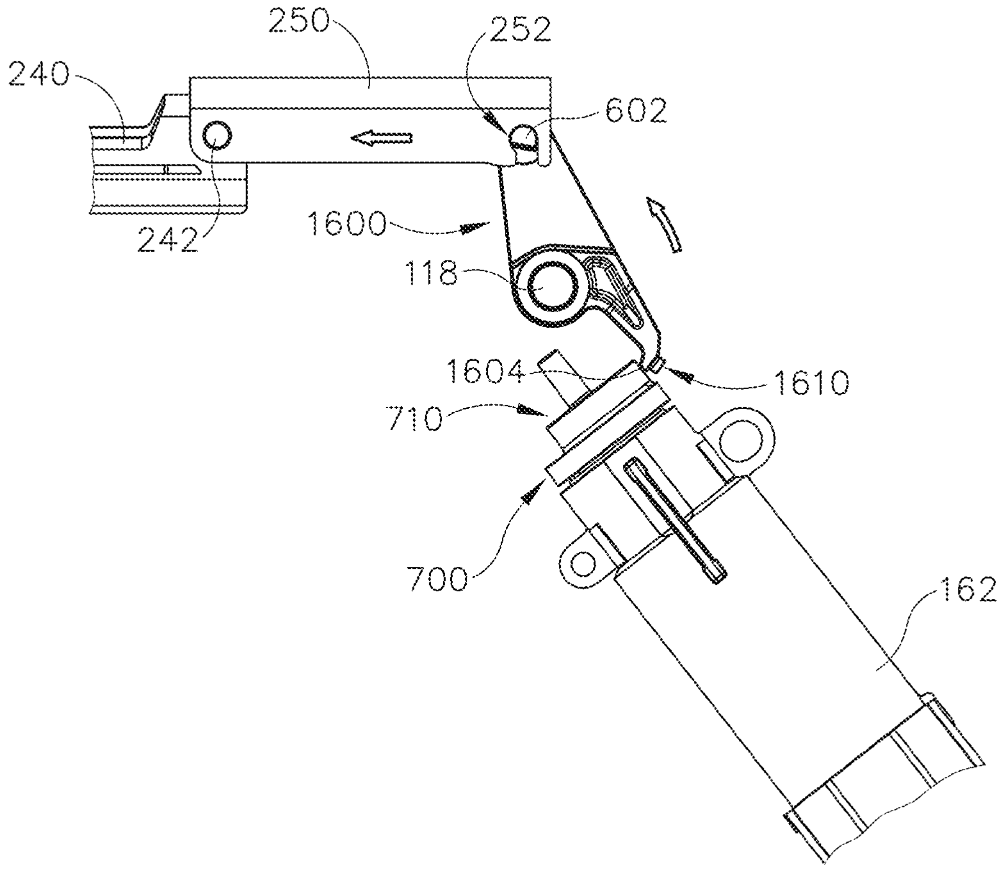
FIG. 24B depicts a side elevational view of the stapling head actuation assembly of FIG. 19, with the rotary cam in a second angular position and the cam follower in a second pivotal position.

FIGS. 24A-24B show the general interaction between cam follower (1600) and first and second cam features (710, 720), though this interaction will be described in greater detail below with reference to FIGS. 14A-14D. As cam member (700) is rotated from the position shown in FIG. 24A to the position shown in FIG. 24B, first cam feature (710) bears against first bearing feature (1604) of cam follower (1600), causing cam follower to pivot about pin (118). In the view shown in FIGS. 24A-24B, cam follower (1600) pivots counterclockwise as cam member (700) is rotated from the position shown in FIG. 24A to the position shown in FIG. 24B. As can be seen in the transition from FIG. 24A to FIG. 24B, this counterclockwise pivoting of cam follower (1600) drives drive bracket (250) and stapling head assembly driver (240) distally, thereby actuating stapling head assembly (300). As cam member (700) continues to rotate in the same direction back toward the position shown in FIG. 24A, second cam feature (720) engages and bears against second bearing feature (1610) of cam follower (1600), causing cam follower (1600) to pivot clockwise about pin (118). This clockwise pivoting of cam follower (1600) about pin (118) retracts drive bracket (250) and stapling head assembly driver (240) proximally back toward the position shown in FIG. 24A.

Referring back to FIGS. 22-23, a third cam feature (730) projects outwardly from outer circumferential surface (706). Third cam feature (730) comprises a first surface region (732) and a second surface region (734). First surface region (732) is flat and is oriented generally tangentially relative to outer circumferential surface (706). Second surface region (732) is also flat and is oriented radially outwardly relative to outer circumferential surface (706). Third cam feature (730) is configured to interact with a rocker member (800) as shown in FIGS. 13A-13B. Rocker member (800) comprises an integral pin (802), a bearing member (804), and a paddle (806). Pin (802) is pivotably coupled with the chassis in casing (110), such that rocker member (800) is pivotable within casing (110) about the longitudinal axis defined by pin (802). Bearing member (804) is configured to interact with third cam feature (730) as will be described in greater detail below. Paddle (806) is configured to actuate a switch buttons (192) of a motor stop module (190) as will also be described in greater detail below.

Figure 25A:
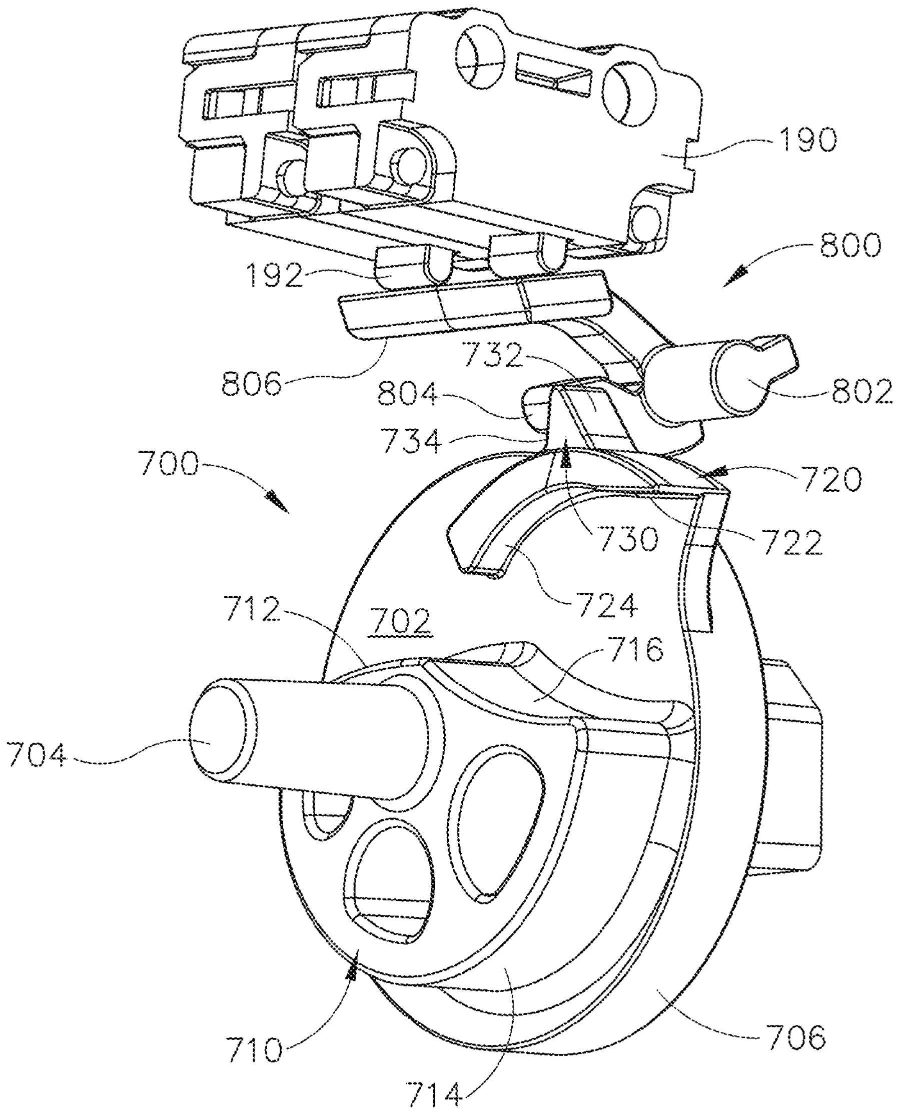
FIG. 25A depicts a perspective view of the rotary cam of FIG. 22, a rocker member, and a stop switch, with the rotary cam in a first angular position and the rocker member in a first pivotal position.
Figure 25B:
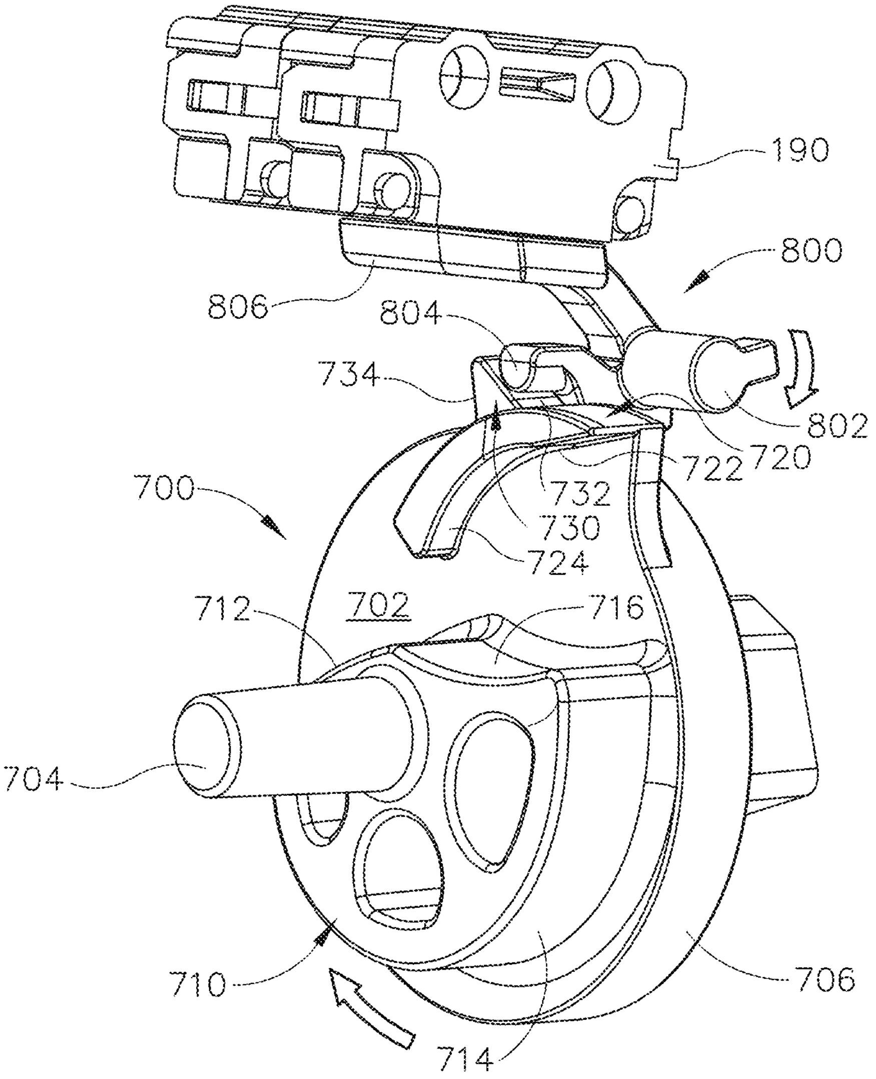
FIG. 25B depicts a perspective view of the rotary cam of FIG. 22, the rocker member of FIG. 25A, and the stop switch of FIG. 25A, with the rotary cam in a fourth angular position and the rocker member in a second pivotal position.

FIG. 25A shows cam member (700) in the same position as shown in FIG. 24A. At this stage, second surface region (734) of third cam feature (730) is adjacent to bearing member (804) of rocker member (800). FIG. 25B shows cam member (700) in a position where cam member (700) has been rotated past the position shown in FIG. 24B and back toward the position shown in FIG. 24A. However, cam member (700) has not completed a full revolution. At the stage shown in FIG. 25B, first surface region (732) has engaged and borne against bearing member (804), thereby pivoting rocker member (800) about the longitudinal axis defined by pin (802). This has caused paddle (806) to actuate switch buttons (192) of motor stop module (190). Motor stop module (190) reverses the polarity of electrical power provided to motor (160) when switch buttons (192) are actuated. This results in stopping activation of motor (160) once an actuation stroke of stapling head assembly (300) has been completed. By way of example only, motor stop module (190) may be configured and operable in accordance with at least some of the teachings of U.S. Pub. No. 2015/0083774, issued as U.S. Pat. No. 9,907,552 on Mar. 6, 2015, the disclosure of which is incorporated by reference herein. Other suitable configurations will be apparent to those of ordinary skill in the art in view of the teachings herein.

Figure 26A:
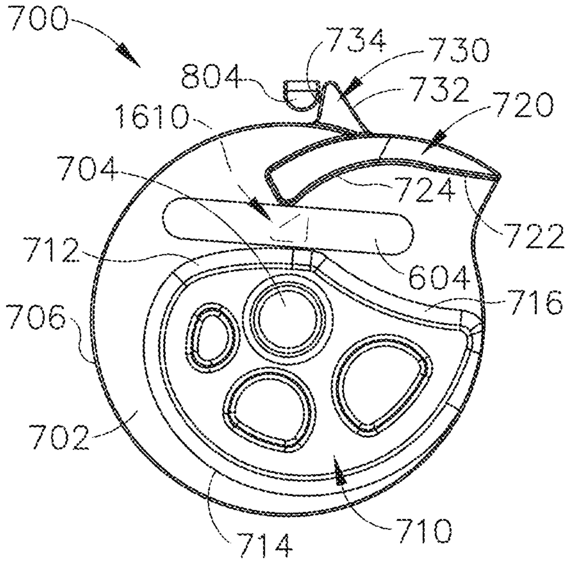
FIG. 26A depicts a schematic end view of the rotary cam of FIG. 22, the cam follower of FIG. 20, and the rocker member of FIG. 25A, with the rotary cam in the first angular position, the cam follower in the first pivotal position, and the rocker member in the first pivotal position.
Figure 26B:
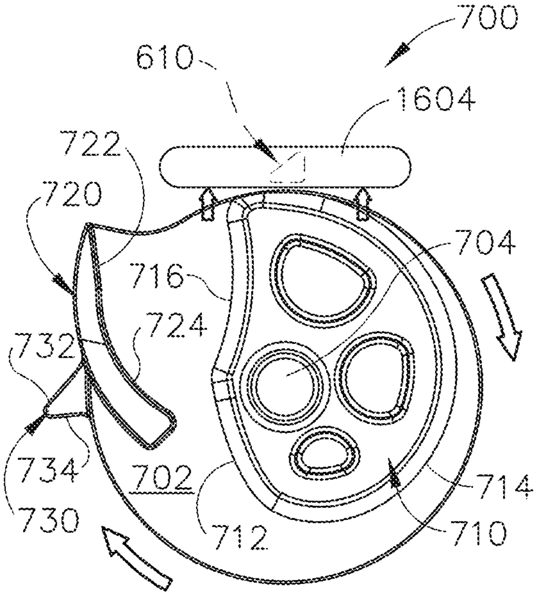
FIG. 26B depicts a schematic end view of the rotary cam of FIG. 22 and the cam follower of FIG. 20, with the rotary cam in the second angular position, the cam follower in the second pivotal position, and the rocker member of FIG. 25A in the first pivotal position.

FIGS. 26A-26D schematically depict the interaction between cam member (700), features of cam follower (1600), and features of rocker member (800) as cam member (700) rotates. It should be understood that the rotation of cam member (700) throughout the stages shown in FIGS. 26A-26D is driven by motor (160) and gearbox (162). FIG. 26A shows cam member (700) in the same position as shown in FIGS. 24A and 25A. At this stage, first bearing feature (1604) of cam follower (1600) is positioned on first surface region (712) and bearing member (804) or rocker member (800) is adjacent to second surface region (734) of third cam feature (730). Also at this stage, knife member (340) and staple driver member (350) are in proximal positions, such that stapling head assembly (300) is in a non-actuated state. As cam member (700) is rotated to the position shown in FIG. 26B, second surface region (714) bears against bearing member (1604), thereby driving bearing member (1604) upwardly. This causes cam follower (1600) to pivot about pin (118) to the position shown in FIG. 24B. Cam follower (1600) thus drives knife member (340) and staple driver member (350) distally via drive bracket (250) and stapling head assembly driver (240). Stapling head assembly (300) is thus in an actuated state at the stage shown in FIG. 26B. In some versions, cam member (700) rotates through an angular range of approximately 270° in order to transition stapling head assembly (300) from the non-actuated state to the actuated state.

Figure 26C:
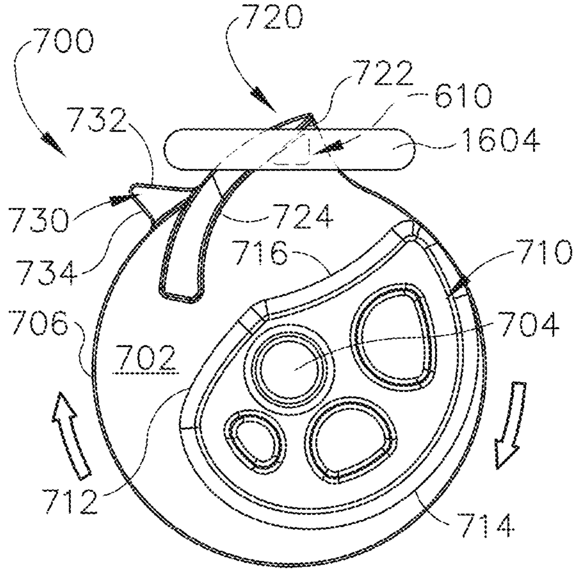
FIG. 26C depicts a schematic end view of the rotary cam of FIG. 22 and the cam follower of FIG. 20, with the rotary cam in a third angular position, the cam follower in the second pivotal position, and the rocker member of FIG. 25A in the first pivotal position.
Figure 26D:
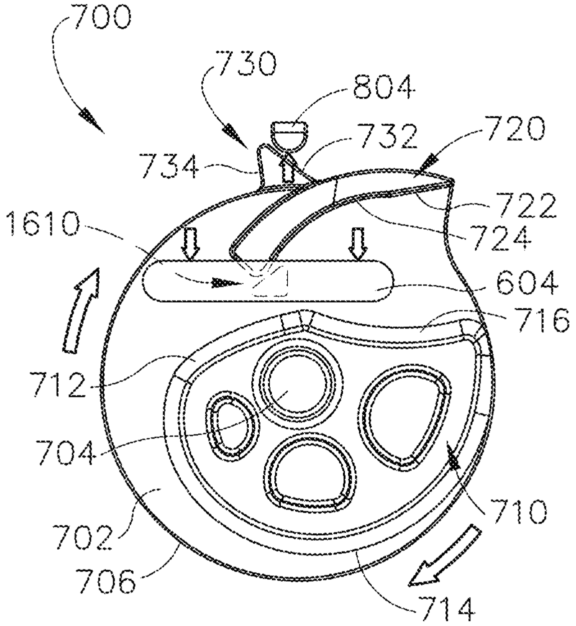
FIG. 26D depicts a schematic end view of the rotary cam of FIG. 22, the cam follower of FIG. 20, and the rocker member of FIG. 25A, with the rotary cam in a fourth angular position, the cam follower in a third pivotal position, and the rocker member in a second pivotal position.

After stapling head assembly (300) has been actuated, cam member (700) continues to rotate to the position shown in FIG. 26C. At this stage, first surface region (722) of second cam member (720) begins to engage curved surface (1616) of second bearing feature (1610) of cam follower (1600). As cam member (700) continues to rotate to the position shown in FIG. 26D, second surface region (724) engages curved surface (1616) of second bearing feature (1610), driving second bearing feature (1610) downwardly. This causes cam follower (1600) to pivot about pin (118) back from the position shown in FIG. 24B toward the position shown in FIG. 24A. Cam follower (1600) thus drives knife member (340) and staple driver member (350) proximally via drive bracket (250) and stapling head assembly driver (240). In addition, first surface region (732) has engaged and borne against bearing member (804), thereby pivoting rocker member (800) about the longitudinal axis defined by pin (802) at the stage shown in FIG. 26D. Rocker member (800) is thus in the same state in FIG. 26D as shown in FIG. 25B. Motor stop module (190) has thus been actuated at the stage shown in FIG. 26D.

It should be understood from the foregoing that cam member (700) is operable to drive knife member (340) and staple driver member (350) distally, then drive knife member (340) and staple driver member (350) proximally and actuate motor stop module (190) by rotating in a single angular direction through the range of motion shown in FIGS. 26A-26D. In the present example, cam member (700) provides the full operational sequence depicted in FIGS. 26A-26D and described above by rotating through an angular range of motion of approximately 355°. More particularly, and by way of further example only, the first 270° of rotation of cam member (700) may provide the distal movement of member (340) and staple driver member (350); while the remaining 85° of rotation of cam member (700) may provide the proximal movement of member (340) and staple driver member (350) and the actuation of motor stop module (190). Other suitable ways in which knife member (340), staple driver member (350), and motor stop module (190) may be actuated will be apparent to those of ordinary skill in the art in view of the teachings herein.

C. Illustrative Clamping and Firing Sequence

Figure 27A:
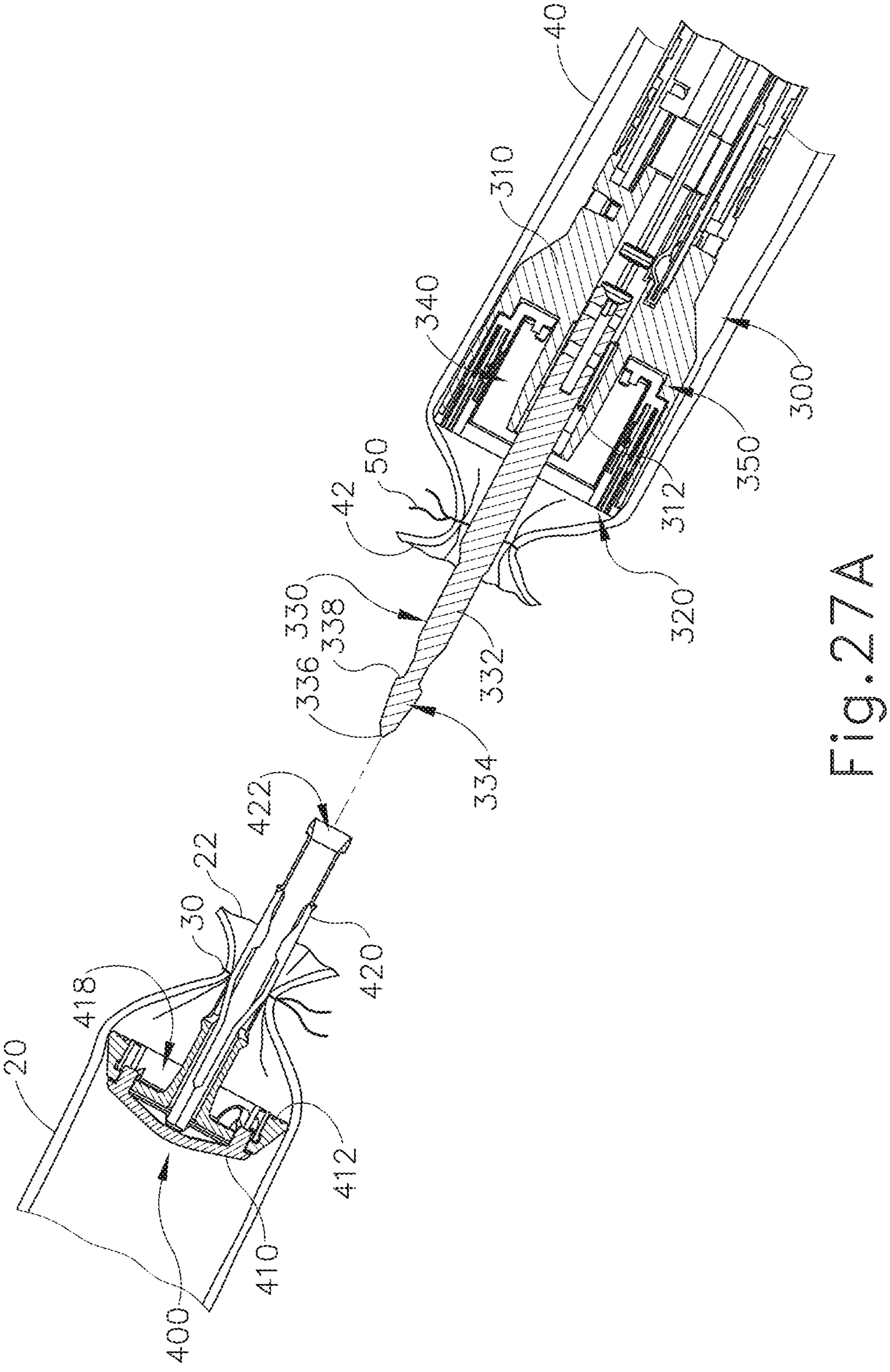
FIG. 27A depicts a cross-sectional side view of the anvil of FIG. 3 positioned within a first section of a digestive tract and the stapling head assembly of FIG. 9 positioned in a second section of the digestive tract, with the anvil separated from the stapling head assembly.
Figure 27B:
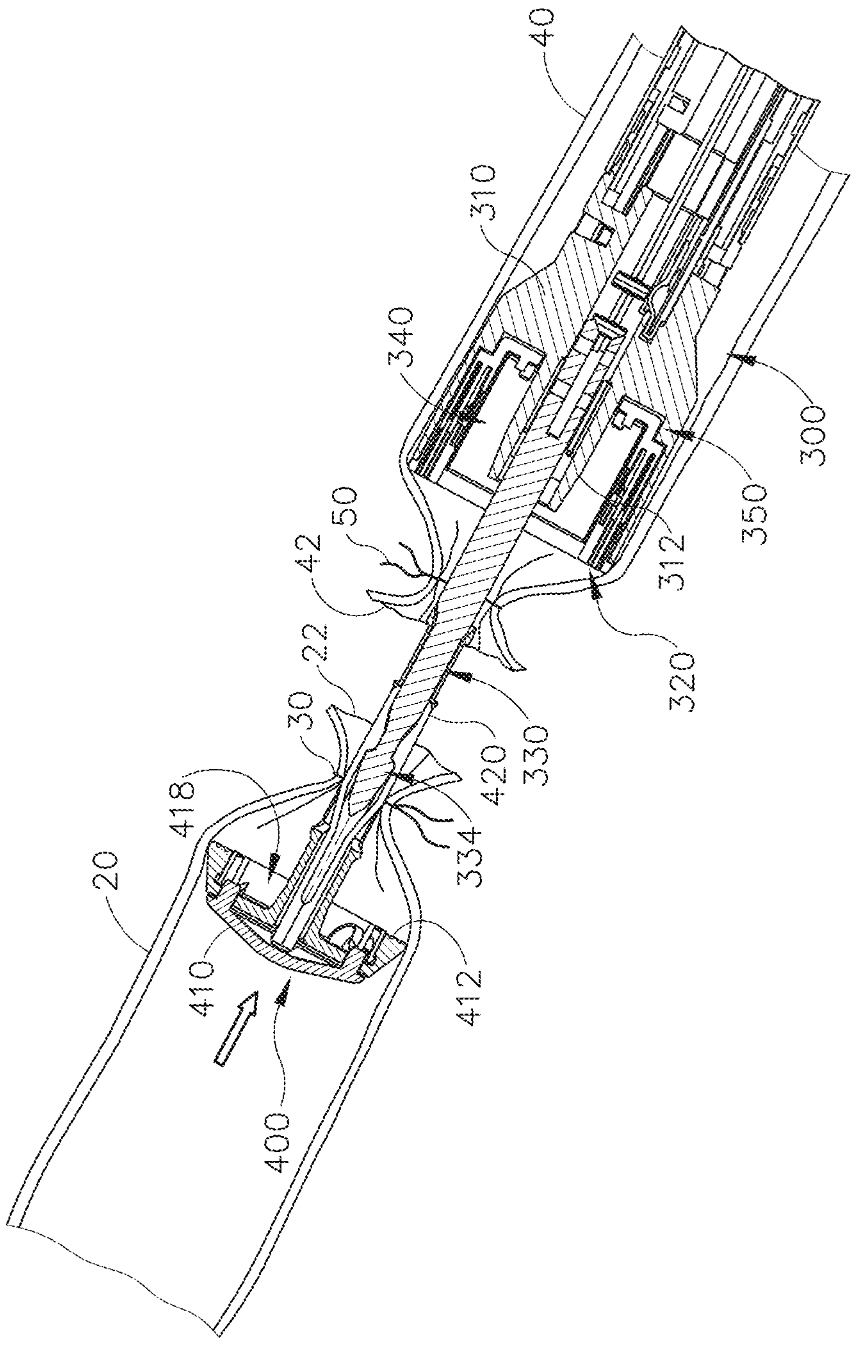
FIG. 27B depicts a cross-sectional side view of the anvil of FIG. 3 positioned within the first section of the digestive tract and the stapling head assembly of FIG. 9 positioned in the second section of the digestive tract, with the anvil secured to the stapling head assembly.
Figure 27C:
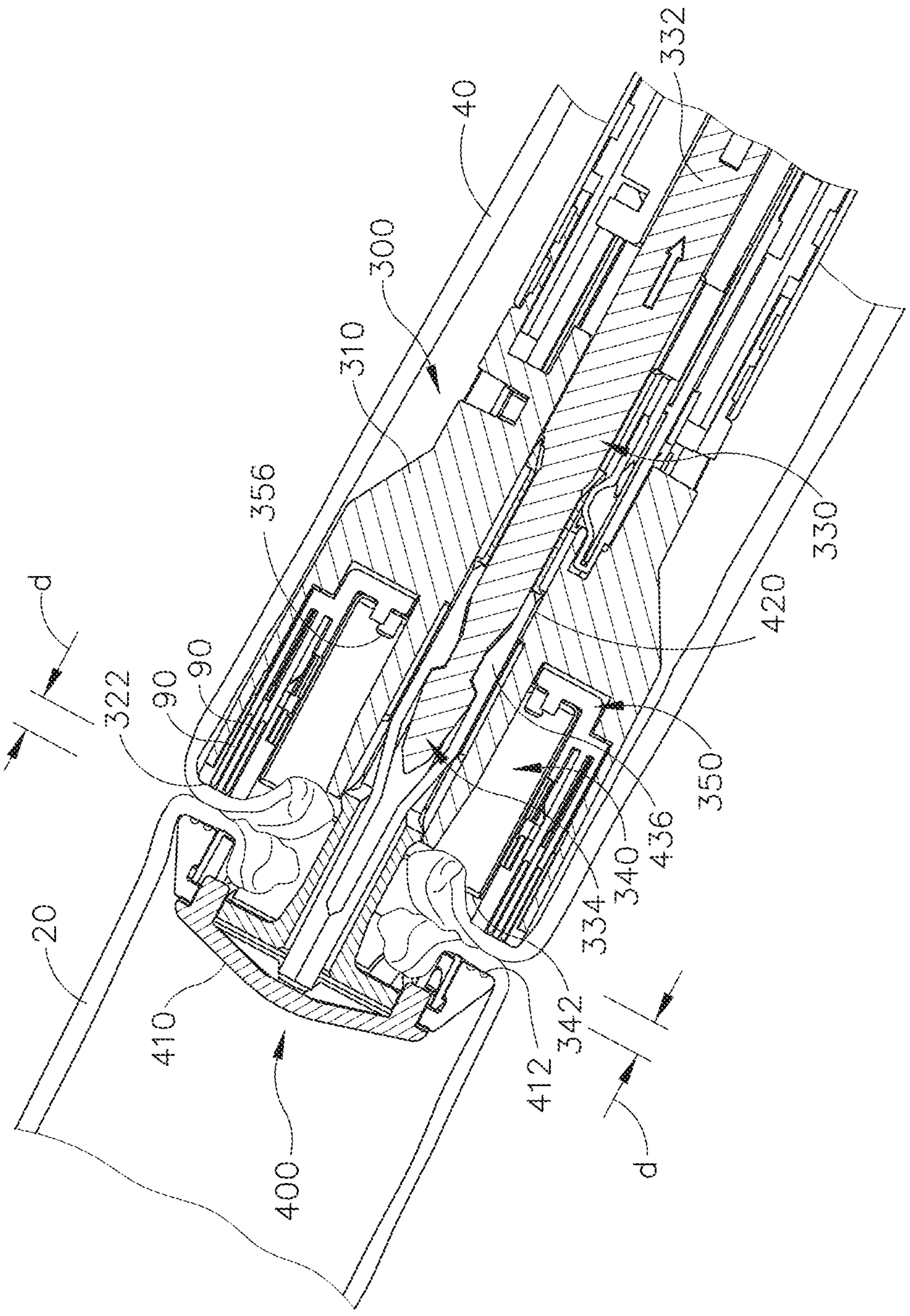
FIG. 27C depicts a cross-sectional side view of the anvil of FIG. 3 positioned within the first section of the digestive tract and the stapling head assembly of FIG. 9 positioned in the second section of the digestive tract, with the anvil retracted toward the stapling head assembly to thereby clamp tissue between the anvil and the stapling head assembly.

FIGS. 27A-27E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. As shown in FIG. 27A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 27A-27E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 27A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). In some other variations, purse-string suture (30) is tightened around the proximal end of shank (420). In some such variations, the proximal end of shank (420) may include a notch or other feature to securely capture purse-string suture (30). Continuing with the present example, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Next, anvil (400) is secured to trocar (330) by inserting trocar (330) into bore (422) as shown in FIG. 27B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 27C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of needle (1526) within user feedback feature (114) to determine whether the gap distance (d) between opposing surfaces (412, 322) of anvil (400) and stapling head assembly (300) is appropriate; and make any necessary adjustments via knob (130).

Figure 27D:
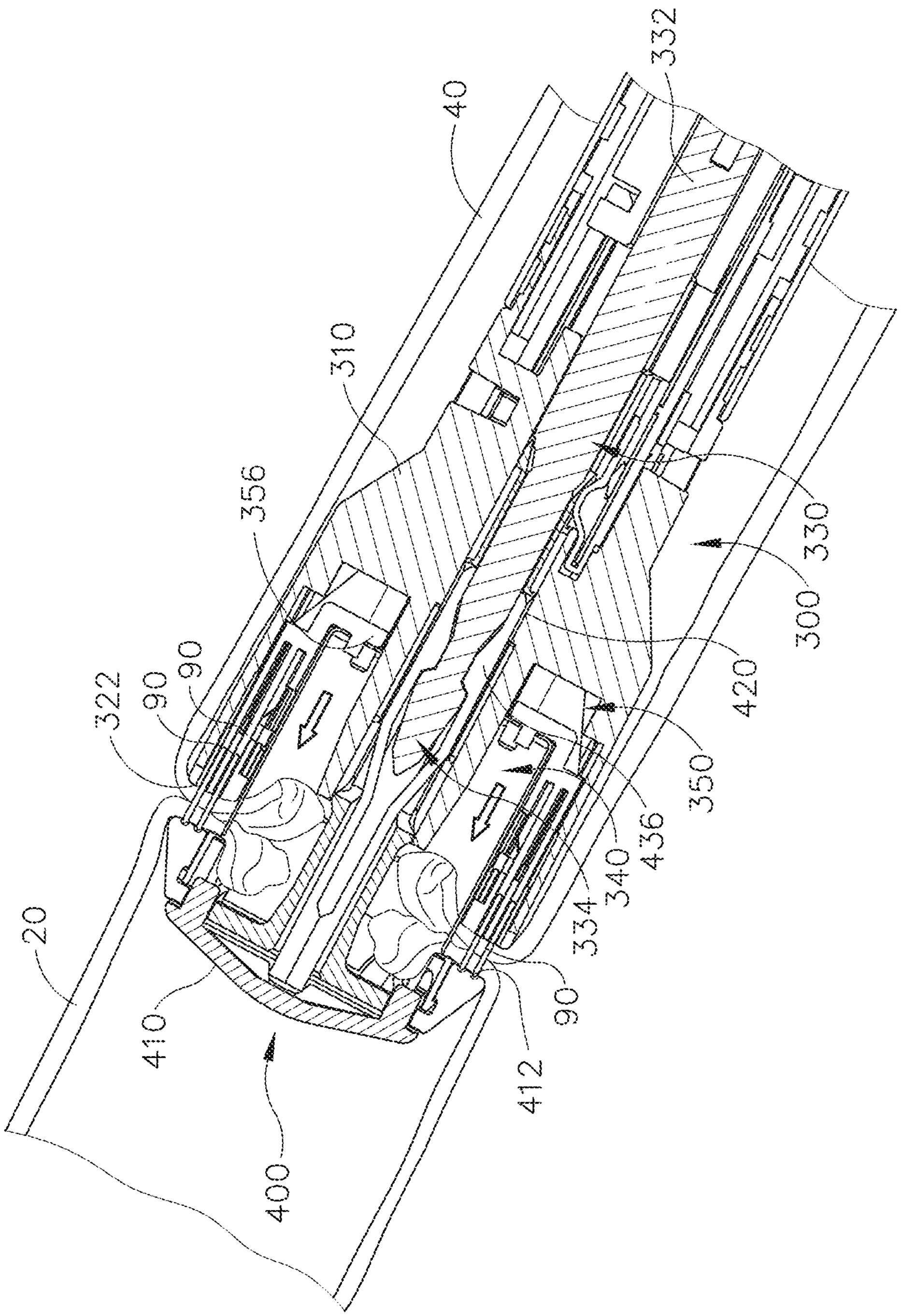
FIG. 27D depicts a cross-sectional side view of the anvil of FIG. 3 positioned within the first section of the digestive tract and the stapling head assembly of FIG. 9 positioned in the second section of the digestive tract, with the stapling head assembly actuated to sever and staple the clamped tissue.

Once the operator has appropriately set the gap distance (d) via knob (130), the operator actuates safety trigger (140) (as shown in FIG. 30D) to enable actuation of firing trigger (150). The operator then actuates firing trigger (150) (as shown in FIG. 30E). This causes paddle (158) to actuate the switch of a motor activation module (180), thereby activating motor to rotate cam member (700) (as shown in FIGS. 26A-26D). This rotation of cam member (700) actuates stapling head assembly (300) by driving knife member (340) and staple driver member (350) distally as shown in FIG. 27D. As knife member (340) translates distally, cutting edge (342) of knife member (340) cuts excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when the knife member (340) completes a full distal range of motion from the position shown in FIG. 27C to the position shown in FIG. 27D. The progressively increasing radius of curvature of second surface region may provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue.

As staple driver member (350) translates distally from the position shown in FIG. 27C to the position shown in FIG. 27D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art; or into a three-dimensional shape as described above with respect to anvil (500). In either case, the formed staples (90) secure the ends of tissue together.

Figure 27E:
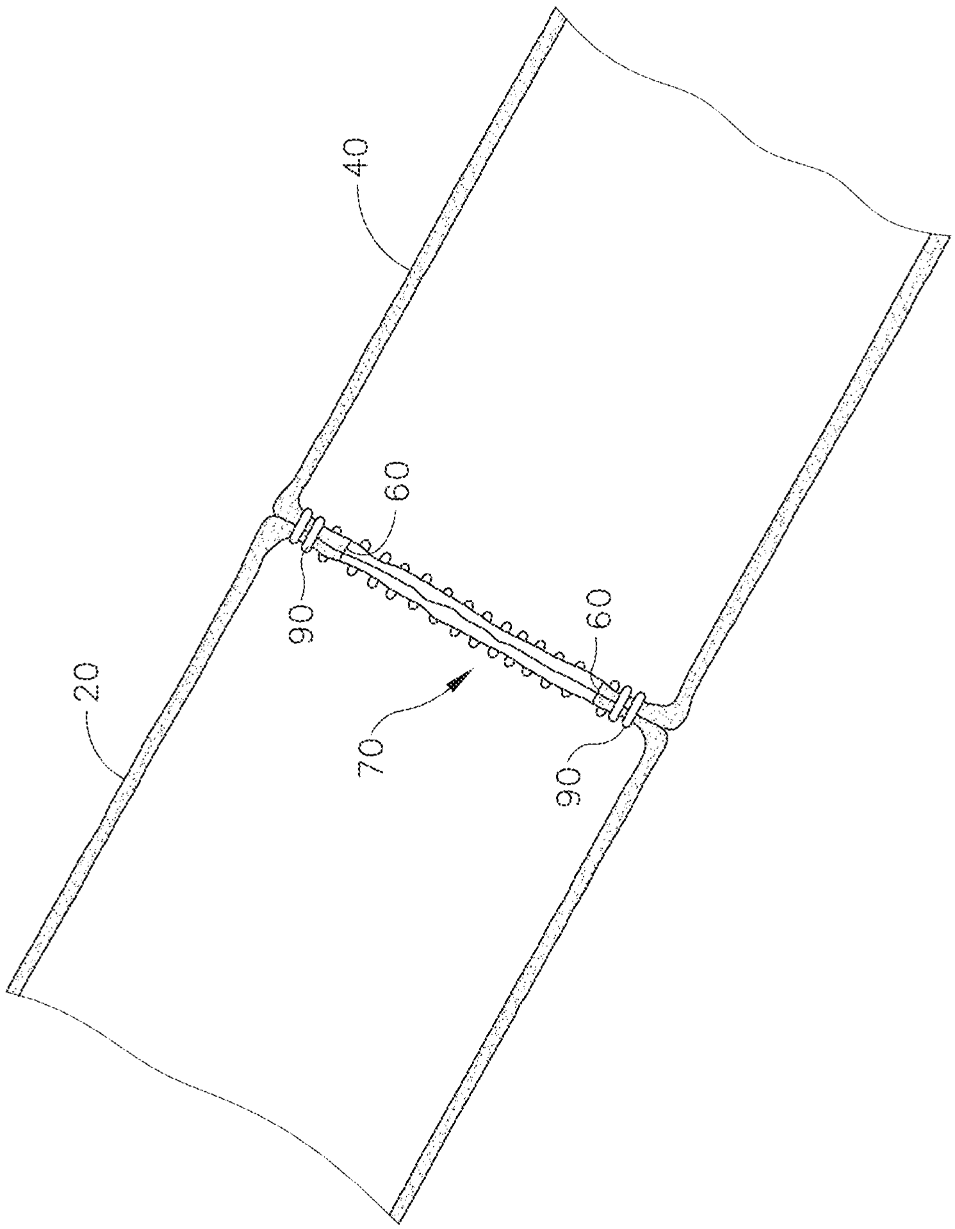
FIG. 27E depicts a cross-sectional side view of the first and second sections of the digestive tract of FIG. 27A joined together at an end-to-end anastomosis.

After the operator has actuated stapling head assembly (300) as shown in FIG. 27D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) is removed, the tubular anatomical structures (20, 40) are left secured together by two annular arrays of staples (90) at an anastomosis (70) as shown in FIG. 27E. The inner diameter of the anastomosis (70) is defined by the severed edge (60) left by knife member (340).

V. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2014, the disclosure of which is incorporated by reference herein, and/or U.S. Pub. No. 2010/0264193, entitled "Surgical Stapling Instrument with An Articulatable End Effector," published Oct. 21, 2010, issued as U.S. Pat. No. 8,408,439 on Apr. 2, 2013, the disclosure of which is incorporated by reference herein.

As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:

(a) a shaft;

(b) an end effector operatively coupled with the shaft, wherein the end effector is selectively actuatable from an open position to a closed position to clamp and staple tissue with a plurality of staples; and (c) a staple firing assembly, including:

(i) a motor, (ii) a cam rotatable by the motor in a first cam direction through each of a first range of motion and a subsequent second range of motion, (iii) a cam follower actuatable by the cam in each of a first follower direction and a second follower direction opposite the first follower direction, and (iv) an end effector driver actuatable by the cam follower in each of a first driver direction and a second driver direction opposite the first driver direction, wherein the cam is rotatable in the first cam direction through the first range of motion to actuate the cam follower in the first follower direction and actuate the end effector driver in the first driver direction to thereby fire staples from the end effector, wherein the cam is further rotatable in the first cam direction through the second range of motion to actuate the cam follower in the second follower direction and actuate the end effector driver in the second driver direction to thereby reset the end effector.

2. The surgical instrument of claim 1, wherein the cam is rotatable about a first rotary axis and the cam follower is rotatable about a second rotary axis offset from the first rotary axis.

3. The surgical instrument of claim 2, wherein the second rotary axis is transverse to the first rotary axis.

4. The surgical instrument of claim 2, wherein the end effector driver is translatable along a longitudinal axis defined by the shaft.

5. The surgical instrument of claim 4, wherein each of the first and second rotary axes is transverse to the longitudinal axis.

6. The surgical instrument of claim 4, wherein the first driver direction comprises a distal direction, wherein the second driver direction comprises a proximal direction.

7. The surgical instrument of claim 1, wherein the staple firing assembly further includes a staple driver housed within the end effector and actuatable by the end effector driver from a home position to a fired position to eject the staples from the end effector as the cam rotates through the first range of motion, wherein the staple driver is configured to reset from the fired position to the home position as the cam rotates through the second range of motion.

8. The surgical instrument of claim 7, wherein the first range of motion comprises at least 270 degrees.

9. The surgical instrument of claim 1, further comprising a body from which the shaft extends away.

10. The surgical instrument of claim 9, wherein the motor, the cam, and the cam follower are housed within the body.

11. The surgical instrument of claim 9, wherein the body comprises a handle configured to be gripped by a user.

12. The surgical instrument of claim 1, wherein the end effector includes a first jaw configured to house a plurality of staples, and a second jaw having a plurality of pockets configured to form the staples.

13. The surgical instrument of claim 12, wherein the second jaw comprises an anvil that is releasably attachable to the first jaw.

14. The surgical instrument of claim 12, wherein the end effector further includes a knife configured to cut tissue.

15. A surgical instrument, comprising:
(a) a shaft;
(b) an end effector operatively coupled with the shaft, wherein the end effector is selectively actuatable from an open position to a closed position to clamp and staple tissue with a plurality of staples; and
(c) a staple firing assembly, including:
(i) a motor,
(ii) a cam rotatable by the motor in a first cam direction through each of a first range of motion and a subsequent second range of motion,
(iii) a cam follower rotatable by the cam in each of a first follower direction and a second follower direction opposite the first follower direction, and
(iv) an end effector driver translatable by the cam follower in each of a distal driver direction and a proximal driver direction,
wherein the cam is rotatable in the first cam direction through the first range of motion to pivot the cam follower in the first follower direction and translate the end effector driver in the distal driver direction to thereby fire staples from the end effector,
wherein the cam is further rotatable in the first cam direction through the second range of motion to pivot the cam follower in the second follower direction and translate the end effector driver in the proximal driver direction to thereby reset the end effector.

16. The surgical instrument of claim 15, wherein the cam is rotatable about a first rotary axis and the cam follower is rotatable about a second rotary axis transverse to the first rotary axis.

17. The surgical instrument of claim 16, wherein the end effector driver is translatable along a longitudinal axis defined by the shaft, wherein each of the first and second rotary axes is transverse to the longitudinal axis.

18. The surgical instrument of claim 15, wherein the staple firing assembly further includes a staple driver housed within the end effector and actuatable by the end effector driver from a home position to a fired position to eject the staples from the end effector as the cam rotates through the first range of motion, wherein the staple driver is configured to reset from the fired position to the home position as the cam rotates through the second range of motion.

19. A surgical instrument, comprising:
(a) body;
(b) a shaft extending away from the body;
(c) an end effector operatively coupled with the shaft, wherein the end effector is selectively actuatable from an open position to a closed position to clamp and staple tissue with a plurality of staples; and
(d) a staple firing assembly, including:
(i) a motor housed within the body,
(ii) a cam housed within the body and rotatable by the motor in a first cam direction through each of a first range of motion and a subsequent second range of motion,
(iii) a cam follower housed within the body and actuatable by the cam in each of a first follower direction and a second follower direction opposite the first follower direction, and
(iv) an end effector driver actuatable by the cam follower in each of a first driver direction and a second driver direction opposite the first driver direction,
wherein the cam is rotatable in the first cam direction through the first range of motion to actuate the cam follower in the first follower direction and actuate the end effector driver in the first driver direction to thereby fire staples from the end effector,
wherein the cam is further rotatable in the first cam direction through the second range of motion to actuate the cam follower in the second follower direction and actuate the end effector driver in the second driver direction to thereby reset the end effector.

20. The surgical instrument of claim 19, wherein the cam follower is rotatably coupled with the body and is rotatable in each of the first and second follower directions.

* * * * *